United States Patent
Kannan et al.

(10) Patent No.: US 11,447,550 B2
(45) Date of Patent: Sep. 20, 2022

(54) PEPTIDES FOR MOLECULAR DETECTION OF PD-L1

(71) Applicant: THE CURATORS OF THE UNIVERSITY OF MISSOURI, Columbia, MO (US)

(72) Inventors: Raghuraman Kannan, Columbia, MO (US); Charles Caldwell, Jr., Columbia, MO (US); Vitukudi Narayanaiyengar Balaji, Columbia, MO (US); Govardhan Aadharsh Balaji, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 659 days.

(21) Appl. No.: 16/338,944

(22) PCT Filed: Sep. 27, 2017

(86) PCT No.: PCT/US2017/053798
§ 371 (c)(1),
(2) Date: Apr. 2, 2019

(87) PCT Pub. No.: WO2018/067361
PCT Pub. Date: Apr. 12, 2018

(65) Prior Publication Data
US 2020/0325231 A1    Oct. 15, 2020

Related U.S. Application Data

(60) Provisional application No. 62/545,103, filed on Aug. 14, 2017, provisional application No. 62/404,030, filed on Oct. 4, 2016.

(51) Int. Cl.
C07K 16/28    (2006.01)
G01N 33/533   (2006.01)
(Continued)

(52) U.S. Cl.
CPC ...... *C07K 16/2827* (2013.01); *A61K 49/0032* (2013.01); *A61K 49/0056* (2013.01);
(Continued)

(58) Field of Classification Search
CPC .................. C07K 16/2827; C07K 1/13; C07K 14/70532; C07K 2319/60; C07K 2319/74;
(Continued)

(56) References Cited

U.S. PATENT DOCUMENTS

| | | | |
|---|---|---|---|
| 2014/0294898 A1* | 10/2014 | Miller | A61P 31/16 424/278.1 |
| 2015/0175660 A1 | 6/2015 | Ioannides et al. | |
| 2016/0039903 A1* | 2/2016 | Ring | A61K 48/00 514/19.3 |

FOREIGN PATENT DOCUMENTS

| | | | |
|---|---|---|---|
| WO | 2015/005500 A1 | 1/2015 | |
| WO | WO-2016022994 A2 * | 2/2016 | A61K 35/17 |

OTHER PUBLICATIONS

Chen et al., "Molecular Pathways: Next-Generation Immunotherapy—Inhibiting Programmed Death—Ligan 1 and Programmed Death-1", Clin Cancer Res, Dec. 15, 2012, pp. 6580-6587.
(Continued)

*Primary Examiner* — Jennifer Wecker
*Assistant Examiner* — Michael Paul Shimek
(74) *Attorney, Agent, or Firm* — Thompson Coburn LLP; William A. Holtz

(57) ABSTRACT

This disclosure relates to synthetic ligands for detecting PD-L1 in a sample or subject. The ligand can be labeled with a variety of detectable labels allowing of visualization and quantification. The ligand provides an alternative PD-L1 binding molecule with advantages over current antibody technologies for detecting PD-L1.

20 Claims, 30 Drawing Sheets

Specification includes a Sequence Listing.

(51) Int. Cl.
| | |
|---|---|
| G01N 33/574 | (2006.01) |
| G01N 33/52 | (2006.01) |
| G01N 33/53 | (2006.01) |
| G01N 33/60 | (2006.01) |
| C07K 1/13 | (2006.01) |
| C07K 14/705 | (2006.01) |
| A61K 49/00 | (2006.01) |
| A61K 51/08 | (2006.01) |
| G01N 15/14 | (2006.01) |
| G01N 33/535 | (2006.01) |
| G01N 33/58 | (2006.01) |

(52) U.S. Cl.
CPC .............. *A61K 51/08* (2013.01); *C07K 1/13* (2013.01); *C07K 14/70532* (2013.01); *G01N 33/52* (2013.01); *G01N 33/53* (2013.01); *G01N 33/533* (2013.01); *G01N 33/574* (2013.01); *G01N 33/57492* (2013.01); *G01N 33/60* (2013.01); *C07K 2319/60* (2013.01); *C07K 2319/74* (2013.01); *G01N 15/14* (2013.01); *G01N 33/535* (2013.01); *G01N 33/582* (2013.01); *G01N 2333/70532* (2013.01)

(58) Field of Classification Search
CPC ........ C07K 14/70503; C07K 14/70596; A61K 49/0032; A61K 49/0056; A61K 51/08; A61K 49/0002; A61K 38/00; G01N 33/52; G01N 33/53; G01N 33/533; G01N 33/574; G01N 33/57492; G01N 33/60; G01N 15/14; G01N 33/535; G01N 33/582; G01N 2333/70532
See application file for complete search history.

(56) References Cited

OTHER PUBLICATIONS

Chen et al., "PD-L1 Expression is Characteristic of a Subset of Aggressive B-Cell Lymphomas and Virus-Associated Malignancies", Clin Cancer Res., Jul. 1, 2013, pp. 3462-3473, vol. 19, No. 13.
Chen et al., "Upregulation of PD-L1 by EGFR Activation Mediates the Immune Escape in EGFR-Driven NSCLC", Journal of Thoracic Oncology, Jun. 2015, pp. 910-923, vol. 10, No. 6.
Cheng ETL., "Co-Development of a Companion Diagnostic for Targeted Cancer Therapy", New Biotechnology, Sep. 2012, pp. 682-688, vol. 29, No. 6, Elsevier.
Garon et al., "Pembrolizumab for the Treatment of Non-Small-Cell Lung Cancer", The New England Journal of Medicine, May 21, 2015, pp. 2018-2028.
Ilie et al., "Comparative Study of the PD-L1 Status Between Surgically Resected Specimens and Matched Biopsies of NSCLC Patients Reveal Major Discordances: A Potential Issue for the Anti-PD-L1 Therapeutic Strategies", Annals of Oncology, Jan. 2016, pp. 147-153, vol. 27, No. 1, Oxford University Press.
Kalia, "Biomarkers for Personalized Oncology: Recent Advances and Future Challenges", Metabolism, 2015, pp. 16-21, vol. 64, Elsevier.
Kerr et al., "Programmed Death Ligand-1 Immunohistochemistry", Arch Pathol Lab Med, Apr. 2016, pp. 326-331, vol. 140.
Kerr et al., "Second ESMO Consensus Conference on Lung Cancer: Pathology and Molecular Biomarkers for Non-Small-Cell Lung Cancer", Annals of Oncology, Apr. 8, 2014, vol. 25, pp. 1681-1690.
La-Beck et al., "Immune Checkpoint Inhibitors: New Insights and Current Place in Cancer Therapy", Pharmacotherapy, Nov. 10, 2015, 14 pages, vol. 35, No. 10.
Mahoney et al., "The Next Immune-Checkpoint Inhibitors: PD-1/PD-L1 Blockade in Melanoma", Clinical Theapeutics, Nov. 4, 2015, pp. 764-782, vol. 37, No. 4.
Naidoo et al., "Immune Checkpoint Blockade", Hematology/Oncology Clinics of North America, Jun. 1, 2014, pp. 585-600, vol. 28, Iss. 3.
Postow et al., "Immune Checkpoint Blockade in Cancer Therapy", Journal of Clinical Oncology, Jun. 10, 2015, pp. 1974-1982, vol. 33, No. 17, New York, New York, USA.
Scheel et al., "Harmonized PD-L1 Immunohistochemistry for Pulmonary Squamous-Cell and Adenocarcinomas", Modern Pathology, Jul. 8, 2016, pp. 1165-1172, vol. 29.
Sholl et al., "Programmed Death Ligand—1 Immunohistochemistry—A New Challenge for Pathologists", Arch Pathol Lab Med, Apr. 2016, pp. 341-344, vol. 140.
Soliman et al., "PD-L1 Expression Is Increased in a Subset of Basal Type Breast Cancer Cells", PLoS ONE, Feb. 2014, pp. 1-10, vol. 9, Iss. 2.
Tumeh et al., "PD-1 Blockade Induces Responses by Inhibiting Adaptive Immune Resistance", Nature, Nov. 27, 2014, 16 pages, vol. 515, Macmillan Publishers Limited.
Usui et al., "Expression of Costimulatory Molecules on Human Retinoblastoma Cells Y-79: Functional Expression of CD40 and B7H1", IOVS, Oct. 2006, pp. 4607-4613, vol. 47, No. 10.
Veras et al., "PD-L1 Expression in Human Placentas and Gestational Trophoblastic Diseases", International Journal Gynecol Pathology, Mar. 2017, pp. 146-153, vol. 36, No. 2.
Zou et al., "PD-L1 (B7-H1) and PD-1 Pathway Blockade for Cancer Therapy: Mechanisms, Response Biomarkers and Combinations", pp. 1-34, PMC, Sep. 2, 2016.

\* cited by examiner

Identification of PDL1 Binding Peptides

SP263

Cy5 Peptide

PEPTIDES FOR MOLECULAR DETECTION OF PD-L1

CROSS-REFERENCE TO RELATED APPLICATIONS

This is a U.S. National Phase application of PCT application PCT/2017/053798, filed on Sep. 27, 2017, which claims the benefit of U.S. Provisional Application Ser. No. 62/545,103, filed Aug. 14, 2017, and U.S. Provisional Application Ser. No. 62/404,030, filed Oct. 4, 2016, each of which are herein incorporated by reference in their entireties.

SEQUENCE LISTING

A sequence listing submitted as a text file via EFS-Web is incorporated herein by reference in its entirety. The text file containing the sequence listing is named "52553_169329_ST25.txt"; its date of creation is Sep. 14, 2017; and its size is 1,682 bytes.

BACKGROUND

Immune checkpoint inhibition has become an important modality for treating cancers, and has demonstrated significant success in recent years (Postow, M. A., Callahan, M. K. & Wolchok, J. D. *Journal of Clinical Oncology* 33, 1974-1982, 2015). By inhibiting immune checkpoints, host immune response recover from tumor evasion. The innate immune response can potentially negate the tumor's ability to resist targeted therapy, eliminating the need for continuous lines of therapy (Tumeh, P. C. et al. *Nature* 515, 568-571, 2014). There are numerous drugs either approved or in the pipeline that target dominant immune checkpoints such as PD-L1 or CTLA4 (Bhardwaj, G., Agrawal, A. & Tyagi, R. *International Journal of Innovation Management* 19, 1540003, 2015; La-Beck, N. M., Jean, G. W., Huynh, C., Alzghari, S. K. & Lowe, D. B. *Pharmacotherapy: The Journal of Human Pharmacology and Drug Therapy* 35, 963-976, 2015). One immune checkpoint of particular interest in human cancers is the interaction between Programmed Cell Death Receptor 1 (PD-1) and its ligand, Programmed Cell Death Ligand 1 (PD-L1) (Zou, W., Wolchok, J. D. & Chen, L. *Science Translational Medicine* 8, 2016). Overexpression of PD-L1 has been reported in many different tumor types, such as melanoma (40-100%), Non-Small Cell Lung Carcinoma (NSCLC) (35%-95%), Glioblastoma (100%), ovarian cancer (33-80%), and colorectal adenocarcinoma (53%) (Chen, D. S., Irving, B. A. & Hodi, F. S. *Clinical Cancer Research* 18, 6580-6587, 2012). PD-L1 expression is characteristic of immune checkpoint evasion, allowing tumor cells to go unrecognized by immune T-cells as foreign. When an activated T-cell recognizes an antigen through binding of T-cell receptor to major histocompatibility complex, other checkpoints such as PD-1:PD-L1 are checked before the T-cell can recognize the cancer cell as foreign. When PD-1 on the T-cell surface and PD-L1 on the tumor surface are allowed to interact, the T-cell will be inhibited from destroying the foreign cell (Naidoo, J., Page, D. B. & Wolchok, J. D. *Hematology/Oncology Clinics of North America* 28, 585-600, 2014) (FIG. 1). Many approved drugs are aimed at binding to and blocking either PD-1 or PD-L1 that stops receptor-ligand binding and will allow the T-cell to continue with killing foreign tumor cells. These drugs have shown therapeutic success in both primary and metastatic cancers (Mahoney, K. M., Freeman, G. J. & McDermott, D. F. *Clinical Therapeutics* 37, 764-782, 2015; Aguiar, P. N. et al. *Immunotherapy* 8, 479-488, 2016); however, not all patients will respond to this kind of therapy based on initial diagnosis. In order to determine which patients should be selected for immune checkpoint therapy, the appropriate diagnostic must be used to determine levels of PD-L1 in the tumor. Patient selection for the therapy depend on the levels of PD-L1 staining in the tissue. Above a certain "cutoff" point on staining pattern, patient would be considered as PD-L1 positive and expected to respond to administered therapy. Some clinical trials confirm that patients with higher expression of PD-L1 levels show increased response to the drug (Garon, E. B. et al. *New England Journal of Medicine* 372, 2018-2028, 2015). In other trials, it is shown that the expression is not a clear predictor for patient's response (Spira, A., et al. *ASCO Annual Meeting Journal of Clinical Oncology, Chicago, Ill.,* 2015). Indeed, diagnosis of PD-L1 expression in patients has proven to be somewhat controversial due to proprietary methods and diagnostic interpretation (Kerr, K. M. & Hirsch, F. R. *Archives of Pathology & Laboratory Medicine* 140, 326-331, 2016; Sholl, L. M. et al. *Archives of Pathology & Laboratory Medicine* 140, 341-344, 2016). PD-L1 assays are being developed in a 'one drug-one assay' method, where assay scoring and guidelines can vary based on the type of drug and diagnostic method used (Scheel, A. H. et al. *Mod Pathol* 29, 1165-1172, 2016), and companion diagnostic development is usually tied to the clinical outcome of the drug (Cheng, S., Koch, W. H. & Wu, L. *New Biotechnology* 29, 682-688, 2012). Drugs such as nivolumab, use PD-L1 companion assays for patient selection. Based on several clinical studies, it is clear that current immunohistochemistry (IHC) diagnostic agents for detecting PD-L1 in patients' tissues suffer from three serious limitations. First, IHC agents for PD-L1 are based on antibodies raised against different clones of PD-L1; even though these IHC agents target the same marker they identify different parts of the marker. Therefore, these agents give different staining pattern based on the clone used. Second, the antibody used for detecting the primary IHC agent bound to the tissue would also be different in these assays resulting in varying performance based on the assay used for diagnosis. Third, the IHC agents were designed and developed by different companies and they would require the use of their own staining equipment and scoring algorithm. For example, Dako's IHC agents used for selecting patients for nivolumab and pembrolizumab, utilize Dako IHC autostainer and their own scoring algorithm. In a similar fashion, for selecting patients for treating with drugs such as Atezolizumab and Durvalumab, Ventana diagnostics utilize Ventana automated IHC platforms and their own scoring algorithm. The data comparing these IHC agents for patients' response, the Blueprint Project—a collaboration of 6 major pharmaceutical companies focused on comparing these tests with patient's response data, is still ongoing. It is worth mentioning that factors such as tumor heterogeneity would not play a role in predicting patient response, as this factor is common in both PD-L1 positive and PD-L1 negative patients. Furthermore, running a different test for each drug evaluated is impractical due to limited tissue from biopsy, turnaround time, and cost. Potential harm to patients can result if inappropriate tests or cutoff levels are used to make treatment decisions (Kalia, M. *Metabolism* 64, S16-S21, 2015). Among all, the PD-L1 marker itself is also somewhat labile and must be evaluated soon after the biopsy. (Kerr, K. M. et al. *Annals of Oncology* 25, 1681-1690, 2014).

Thus, there remains a need to develop additional reagents and methods for detecting PD-L1 to aid in the diagnosis and treatment of cancer.

SUMMARY

One aspect of this disclosure is directed to a detectably labeled synthetic ligand comprising a peptide or peptidomimetic compound. In certain aspects, the peptide or peptidomimetic compound comprises amino acid sidechains following the entire sequential order of the amino acid sequence SEQ ID NO: 1. In certain aspects, the peptide or peptidomimetic compound has a length equal or equivalent to 19 to 39, 19 to 29, 19 to 25, 19 to 23, 19 to 22, or 19 to 21 amino acid residues. In certain aspects, the ligand specifically binds to the programmed death-ligand 1 (PD-L1) protein or a portion and/or fragment thereof. In certain aspects, the ligand is detectably labeled with a detectable label. Numerous detectable labels capable of labeling a peptide or peptidomimetic compound are know in the art and type of detectable is not limiting. Representative detectable labels include fluorescent molecules, radioisotopes, enzyme conjugates, and heterologous epitopes. In certain aspects, the peptide or peptidomimetic compound is attached to the detectable label via an amino acid spacer. In certain aspects, the amino acid spacer is $(GS)_n$, wherein n is, for example, 2 to 10, 2 to 5, or 3 to 5. In certain aspects, the peptide or peptidomimetic compound has a length equal or equivalent to 19 or to 20 amino acid residues. In certain aspects, the ligand is a peptide and the peptide and amino acid spacer consist of the amino acid sequence SEQ ID NO: 2 (RK-10 peptide). In certain aspects, the detectable label is biotin or a fluorescent reporter molecule. In certain aspects, the ligand is selected from the group consisting of the peptide ligand Biotin-$(GS)_3$—SEQ ID NO: 1 (RK-10-Biotin), the peptide ligand Cy5-$(GS)_3$—SEQ ID NO: 1 (RK-10-Cy5), and peptidomimetic compound ligands corresponding to either.

Certain aspects of this disclosure provide for a composition comprising a synthetic ligand the specifically binds PD-L1 as disclosed herein.

Certain aspects of this disclosure provide for a method of detecting PD-L1. In certain such methods aspects, the method comprises: a) contacting a sample with a detectably labeled synthetic ligand and/or a composition disclosed herein; and assaying for the presence of the labeled ligand. In certain aspects, a sample comprises cells from a subject or a cell line. In certain aspects, a sample from a subject is blood or a tissue. In certain aspects, a sample from a subject comprises cancer cells. In certain aspects, the presence of the labeled ligand is detected via immunohistochemistry or flow cytometry. In certain aspects, the presence of the labeled ligand is indicative of the amount of PD-L1 expression in the sample or subject and the method further comprises comparing the amount of PD-L1 expression in the sample or subject against a predetermined standard. In certain aspects, the method further comprises treating the subject's cancer based on the comparison.

Certain aspects of this disclosure provide for a method of detecting PD-L1 in a subject. In certain aspects, the method comprising the steps of: (a) administering a detectably labeled synthetic ligand and/or the composition disclosed herein to the subject; and (b) assaying for the presence of the labeled ligand in said subject. In certain aspects, the location of the labeled ligand in the subject is visualized. In certain aspects, the location of the labeled ligand is indicative of a cancer tumor. In certain aspects, the method further comprises treating the subject's cancer based on the location of the tumor.

Certain aspects of this disclosure provide for a method of making a detectably labeled synthetic ligand for detecting PD-L1. In certain aspects, the method comprises incorporating a detectable label into, or attaching either directly or via a spacer a detectable label to, a peptide or peptidomimetic compound that comprises amino acid sidechains following the entire sequential order of the amino acid sequence SEQ ID NO: 1, wherein the peptide or peptidomimetic compound has a length equal or equivalent to 19 to 39 amino acid residues. In certain aspects, the method comprises synthesizing the peptide or peptidomimetic compound.

Certain aspects of this disclosure provide for an isolated peptide comprising the amino acid sequence SEQ ID NO: 1, wherein the peptide is from 19 to 39 amino acids in length and wherein the peptide comprises at least one non-naturally occurring modification. In certain aspects, the non-naturally occurring modification allows for detection, increases stability, increases binding to PD-L1, or increases biofouling. Certain aspects also provide for a peptidomimetic compound comprising amino acid sidechains following the entire sequential order of the amino acid sequence SEQ ID NO: 1 wherein the peptidomimetic compound has a length equivalent to 19 to 39 amino acid residues.

Certain aspects of this disclosure provide or a kit for detecting PD-L1 comprising a peptide or peptidomimetic compound or composition disclosed herein. In certain aspects, the peptide or peptidomimetic compound is detectably labeled.

BRIEF DESCRIPTION OF THE DRAWINGS/FIGURES

DETAILED DESCRIPTION

Overview

Figure 1:
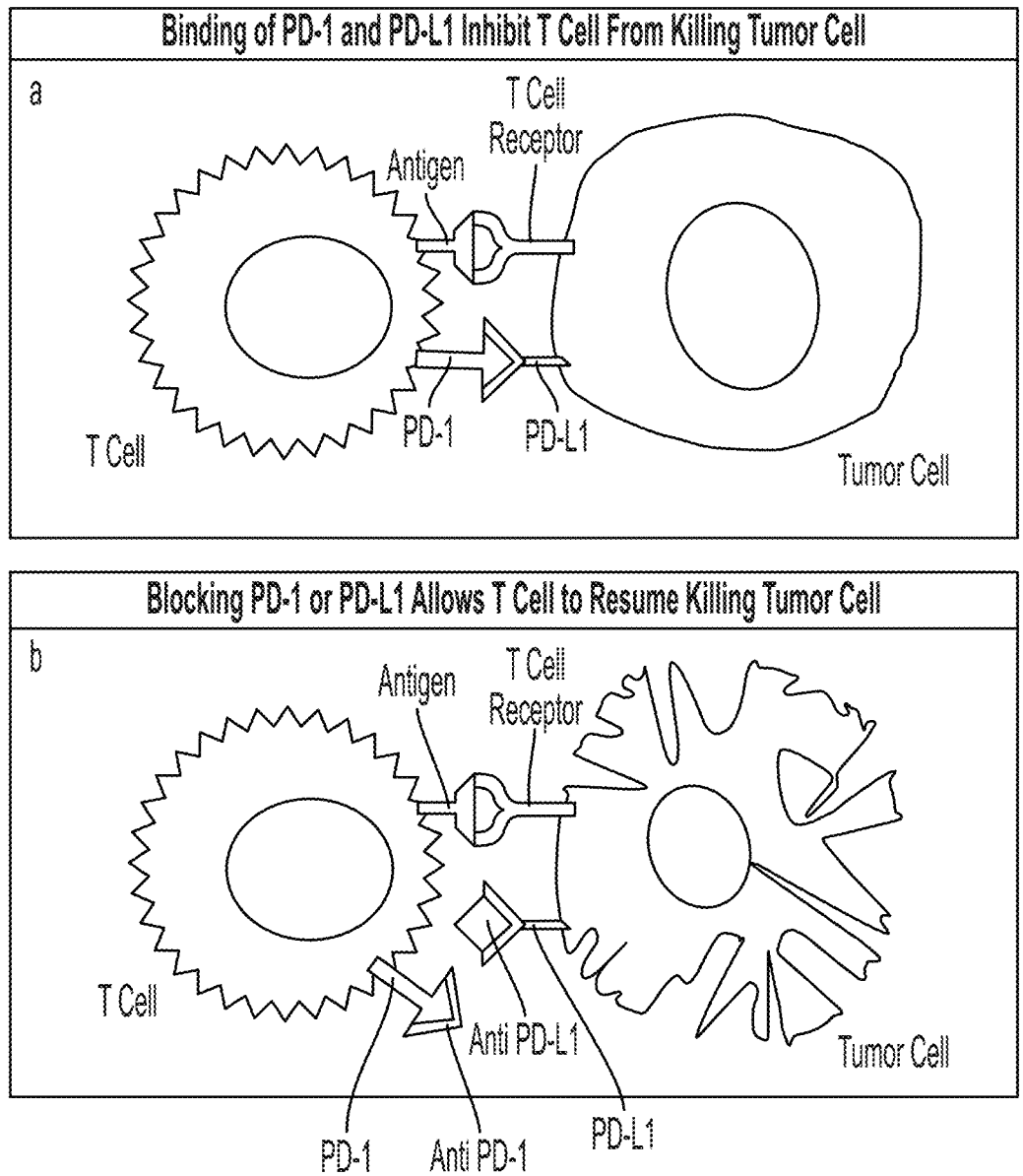
FIG. 1 is a schematic illustrating that binding of PD-1 and PD-L1 inhibits T Cells from killing tumor cells and that blocking of PD-1 and/or PD-L1 allows T Cells to resume killing tumor cells.
Figure 2A:
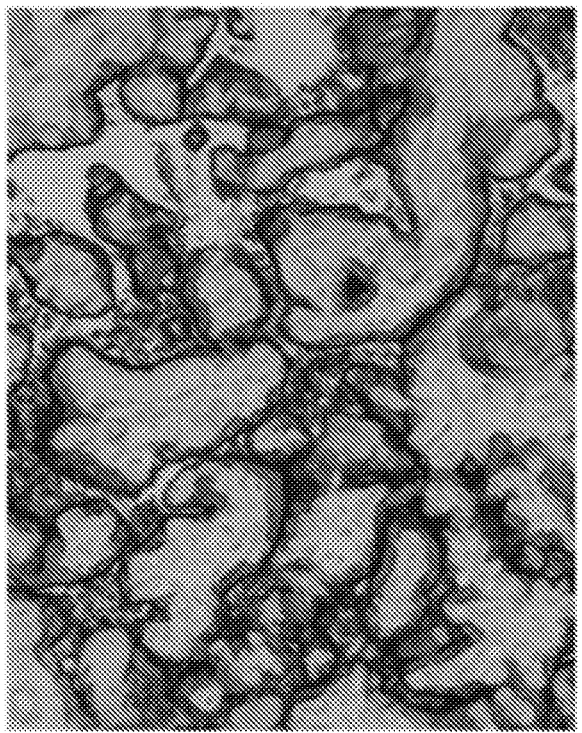
FIG. 2A shows placental tissue IHC staining with a Roche PD-L1 antibody.
Figure 2A:
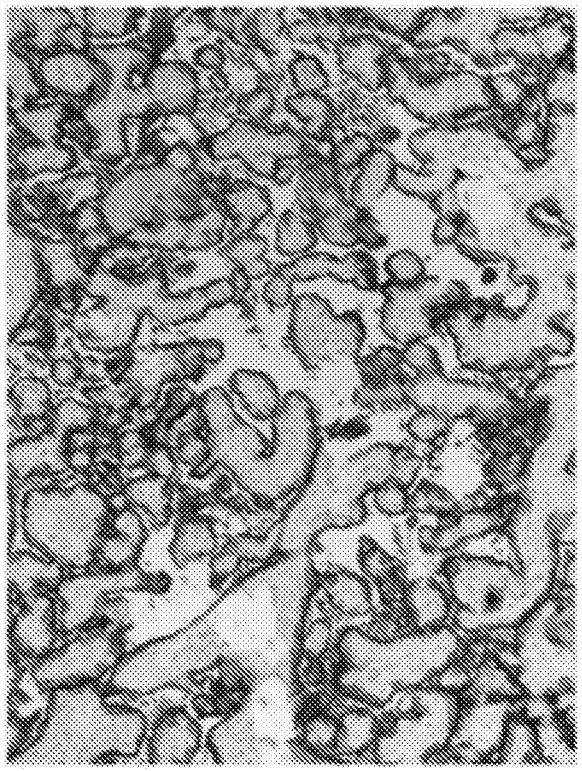
Figure 2B:
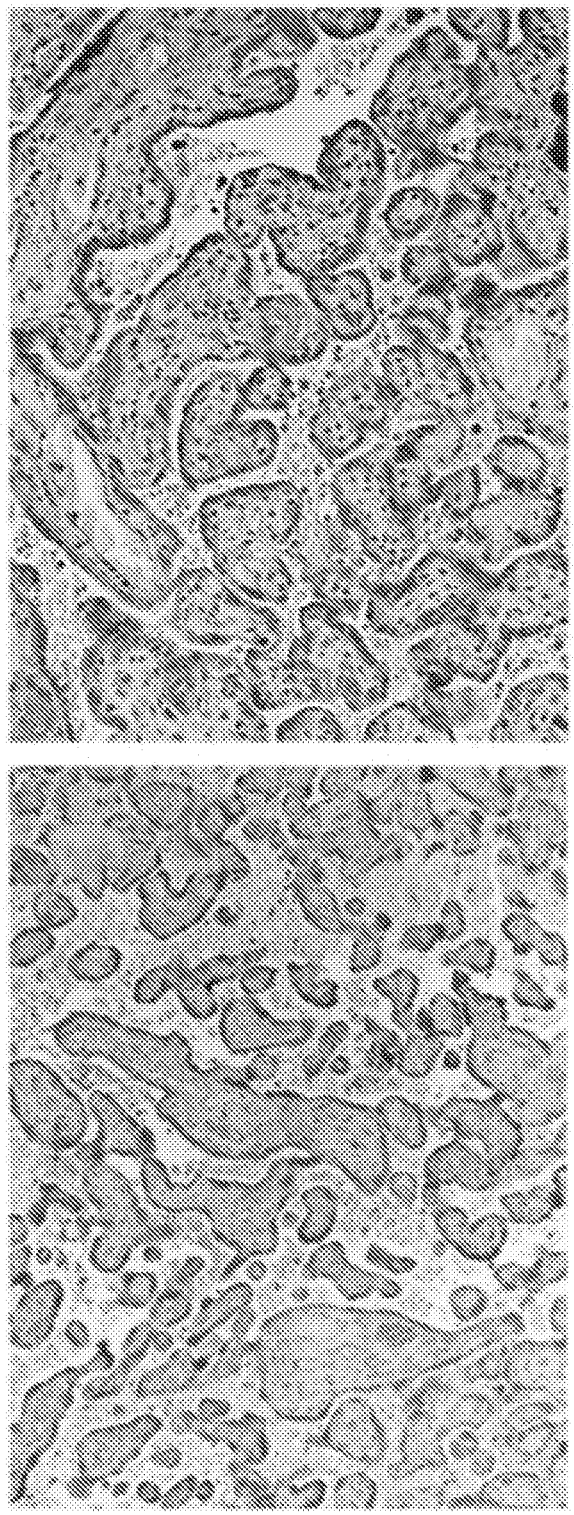
FIG. 2B shows placental tissue IHC staining with a PD-L1 binding peptide disclosed herein.
Figure 2C:
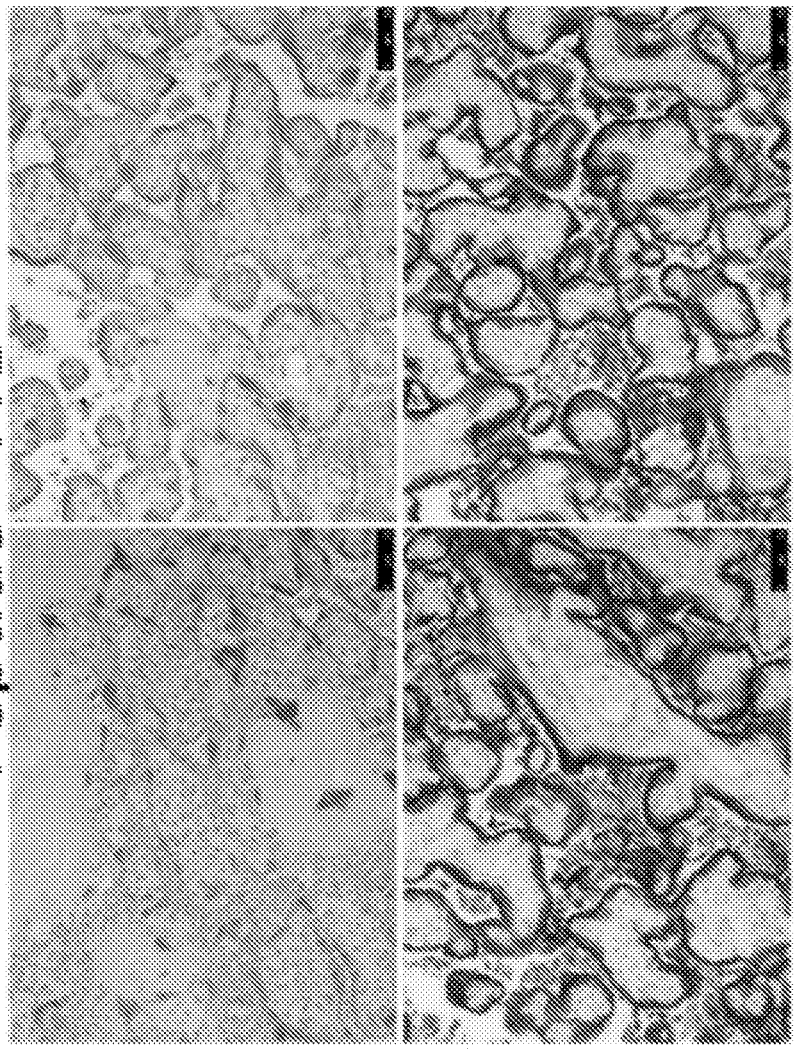
FIG. 2C shows blocking of the Roche antibody using the PD-L1 binding peptide.
Figure 3:
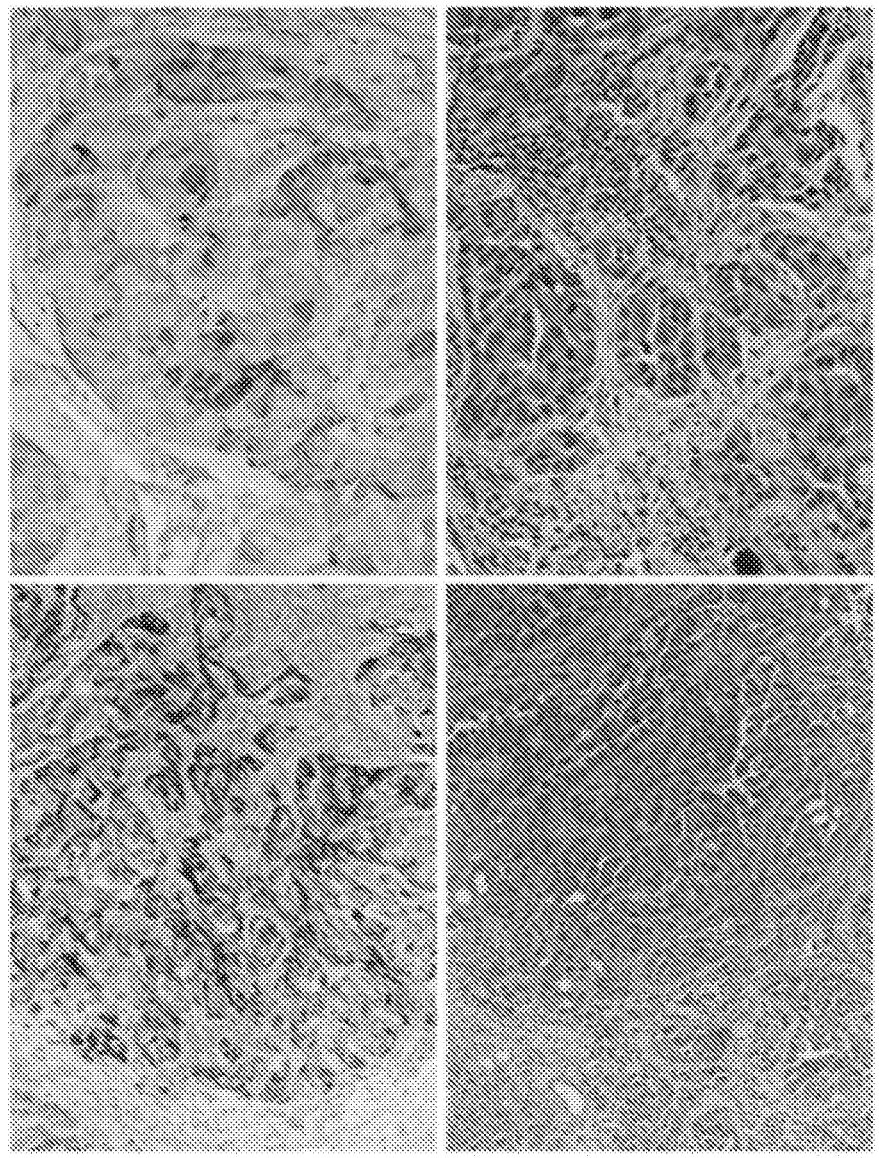
FIG. 3 is a comparison of IHC staining of a subject NSCLC sample, comparing the Roche antibody and a PD-L1 binding peptide.
Figure 4:
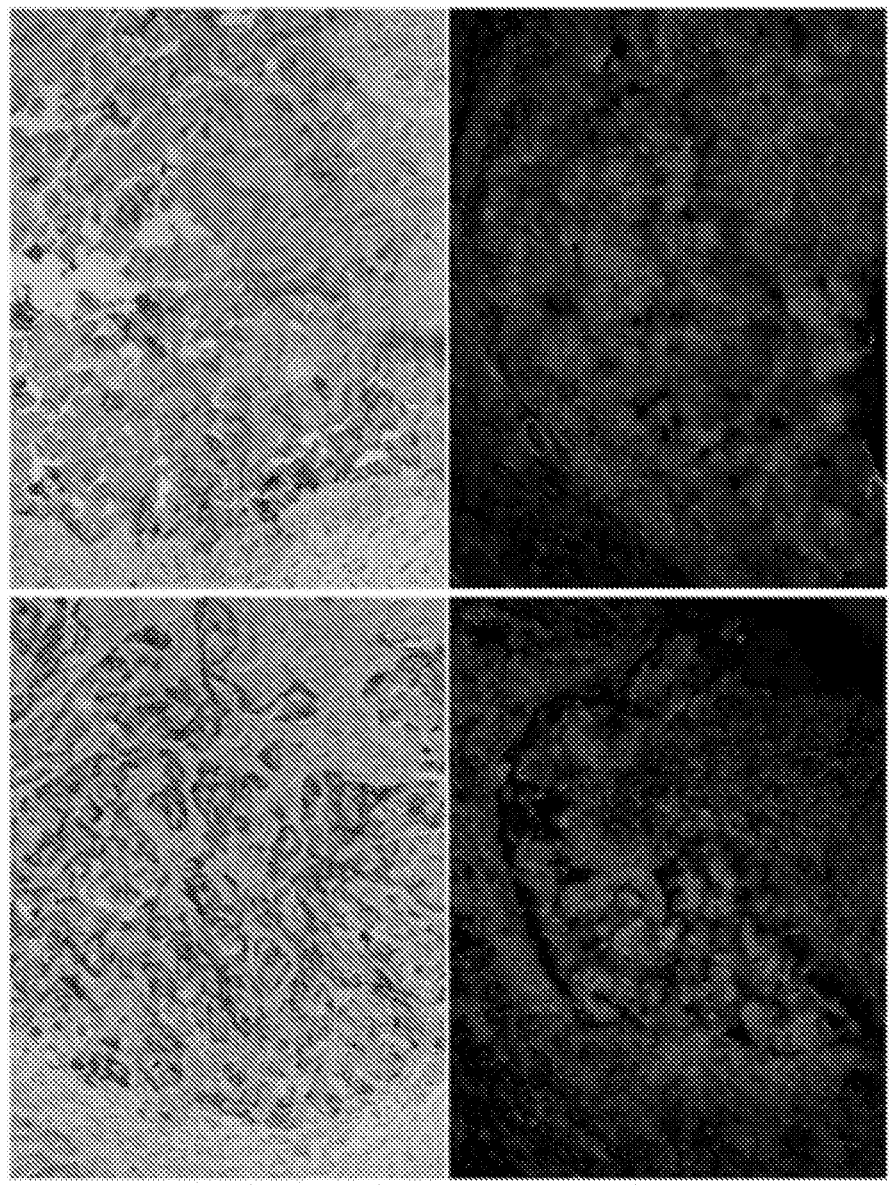
FIG. 4 is a comparison of fluorescent IHC staining of a subject NSCLC sample, comparing the Roche PD-L1 antibody and PD-L1 binding peptide of the disclosure.
Figure 5:
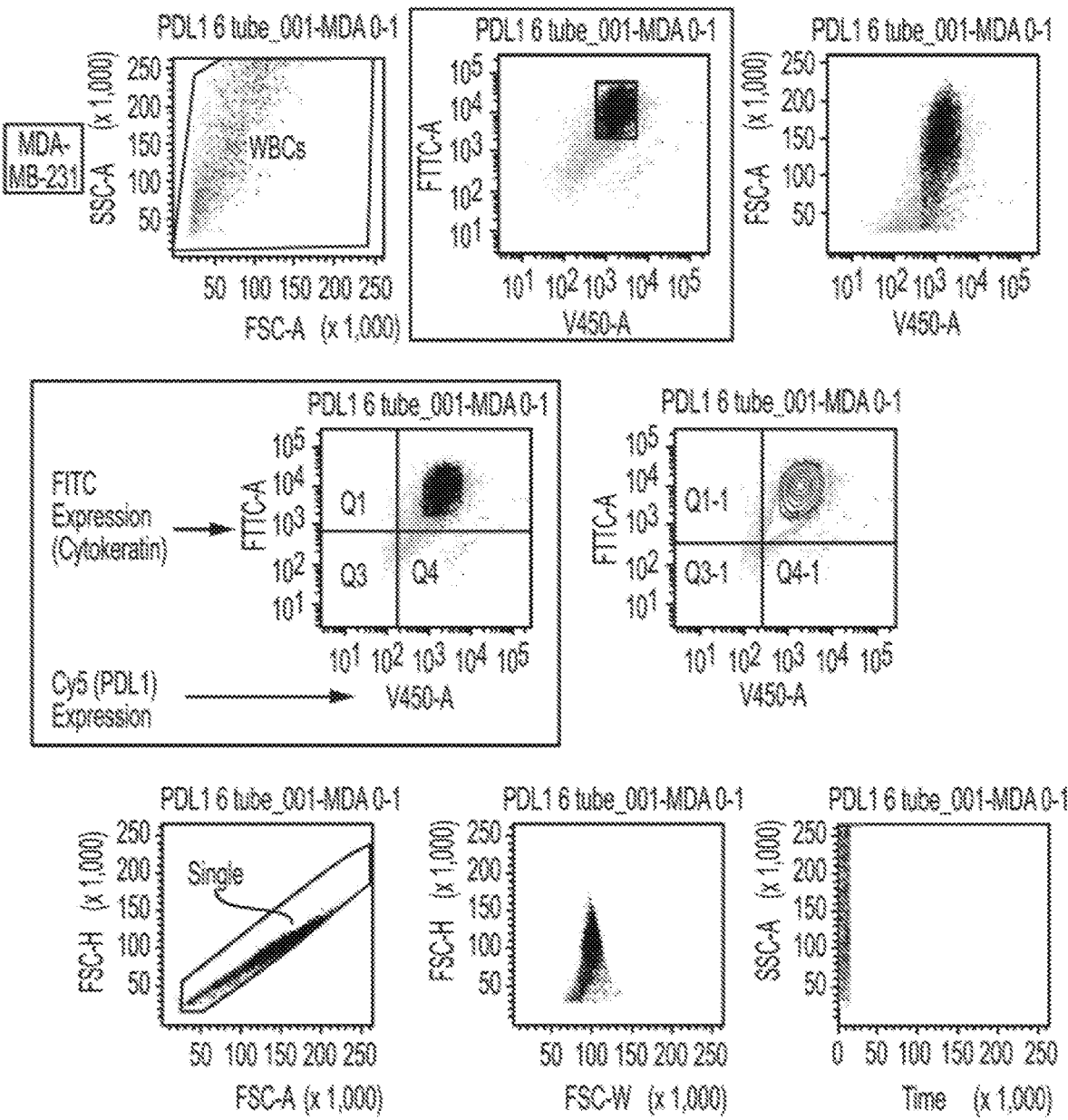
FIG. 5 shows representative flow cytometry analysis of PD-L1 expression in patient tissues using the PD-L1 binding peptide designated RK-10-Cy5 herein.
Figure 5:
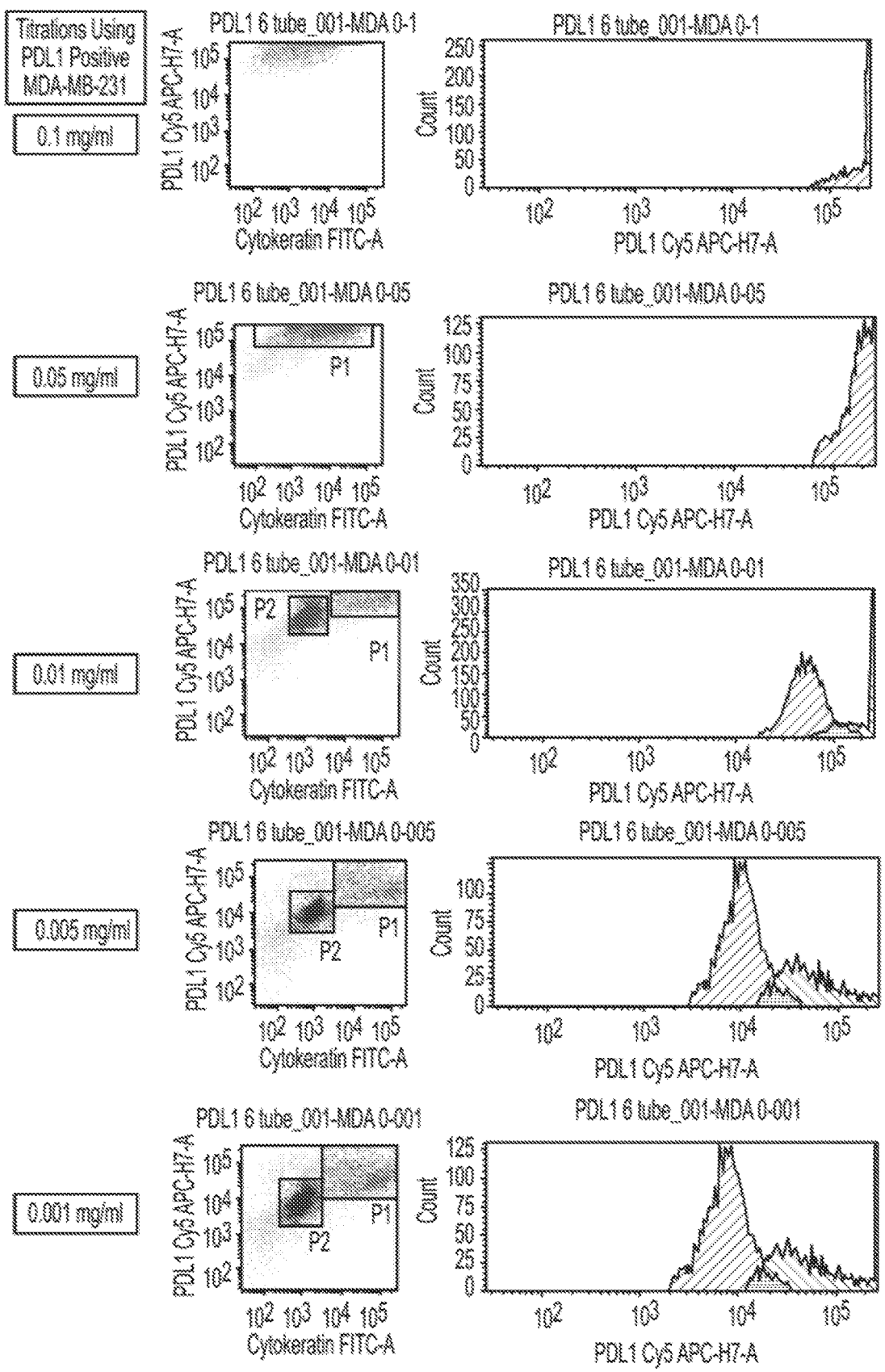
Figure 5:
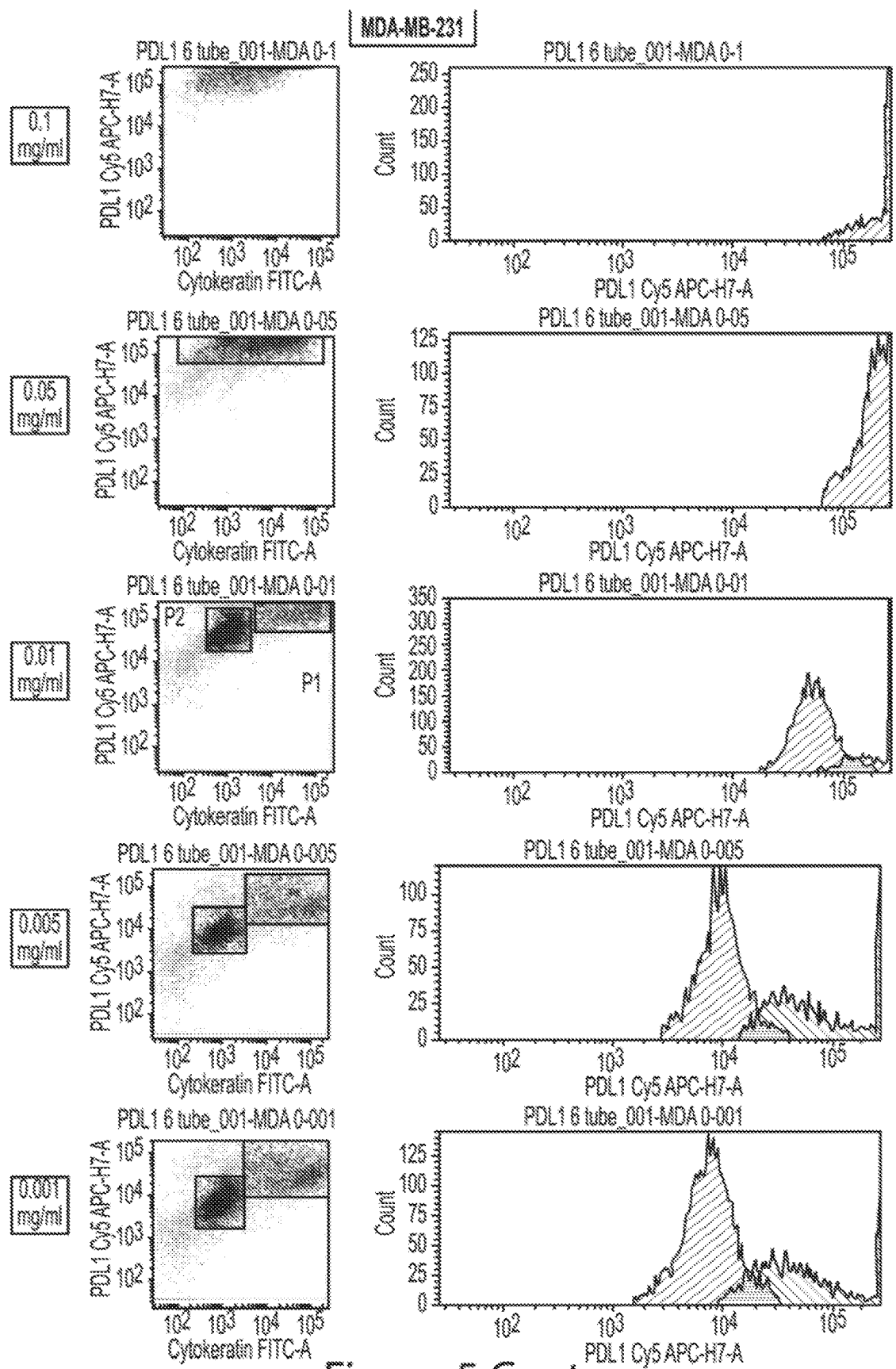
Figure 5:
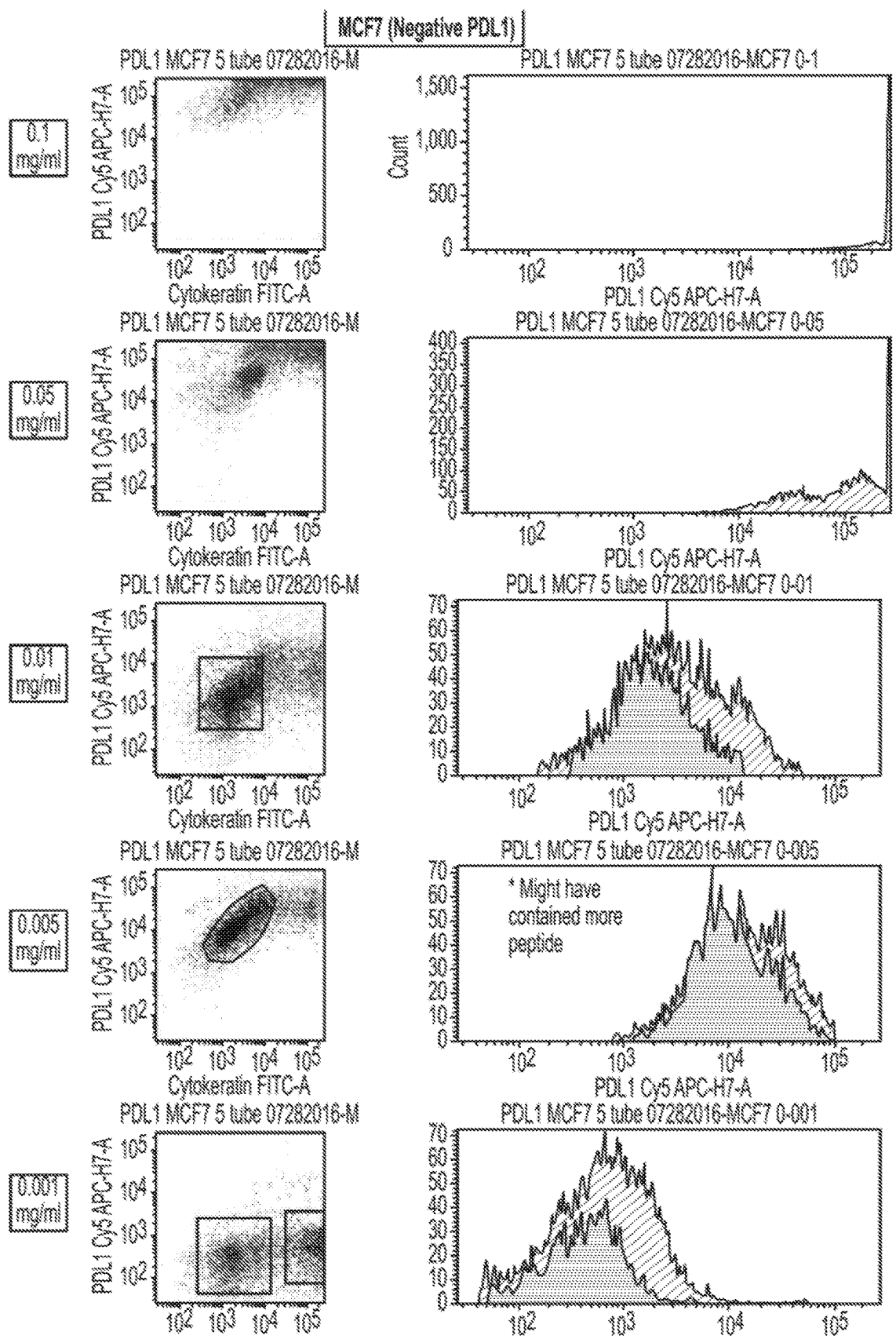
Figure 5:
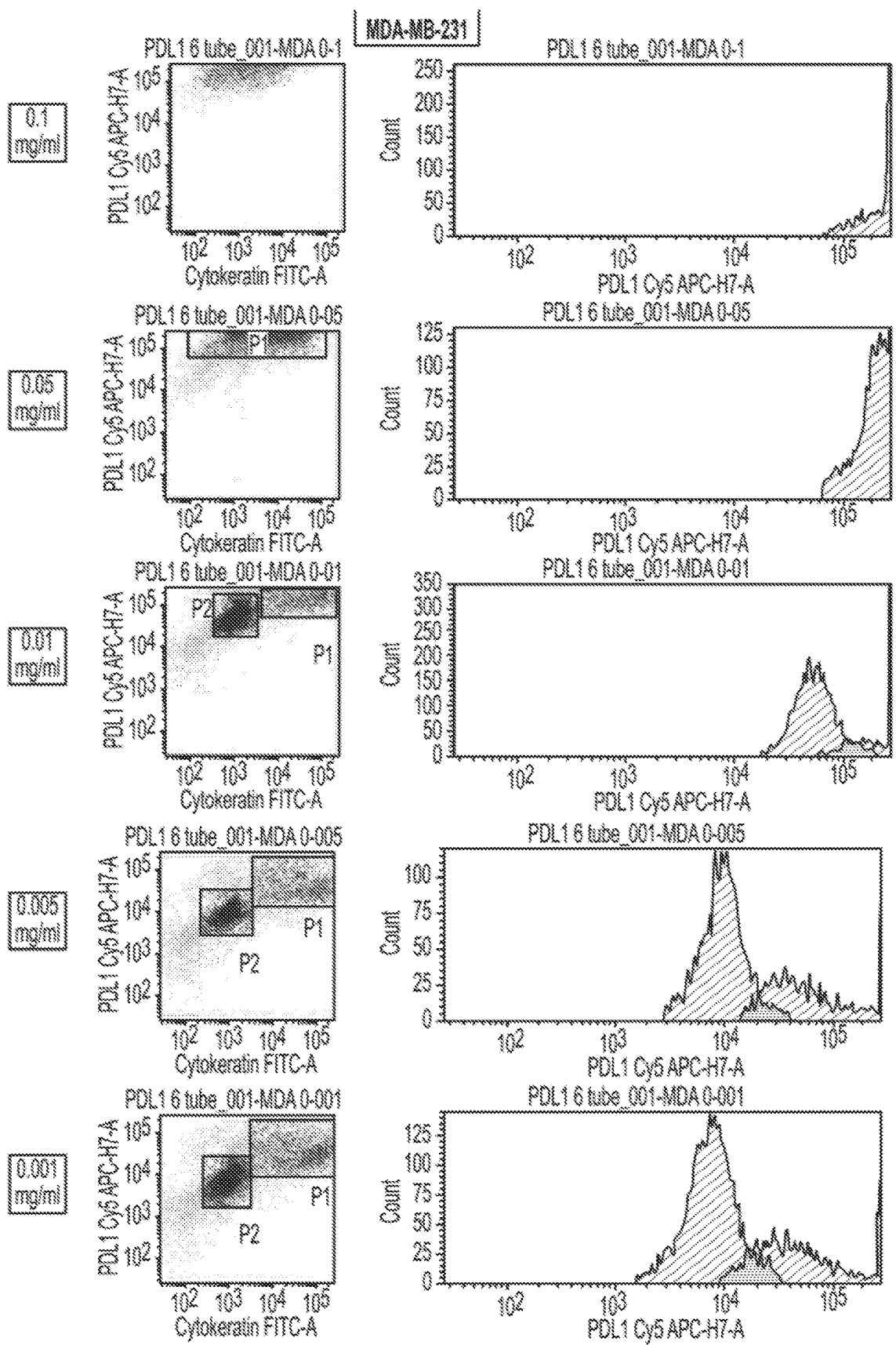
Figure 5:
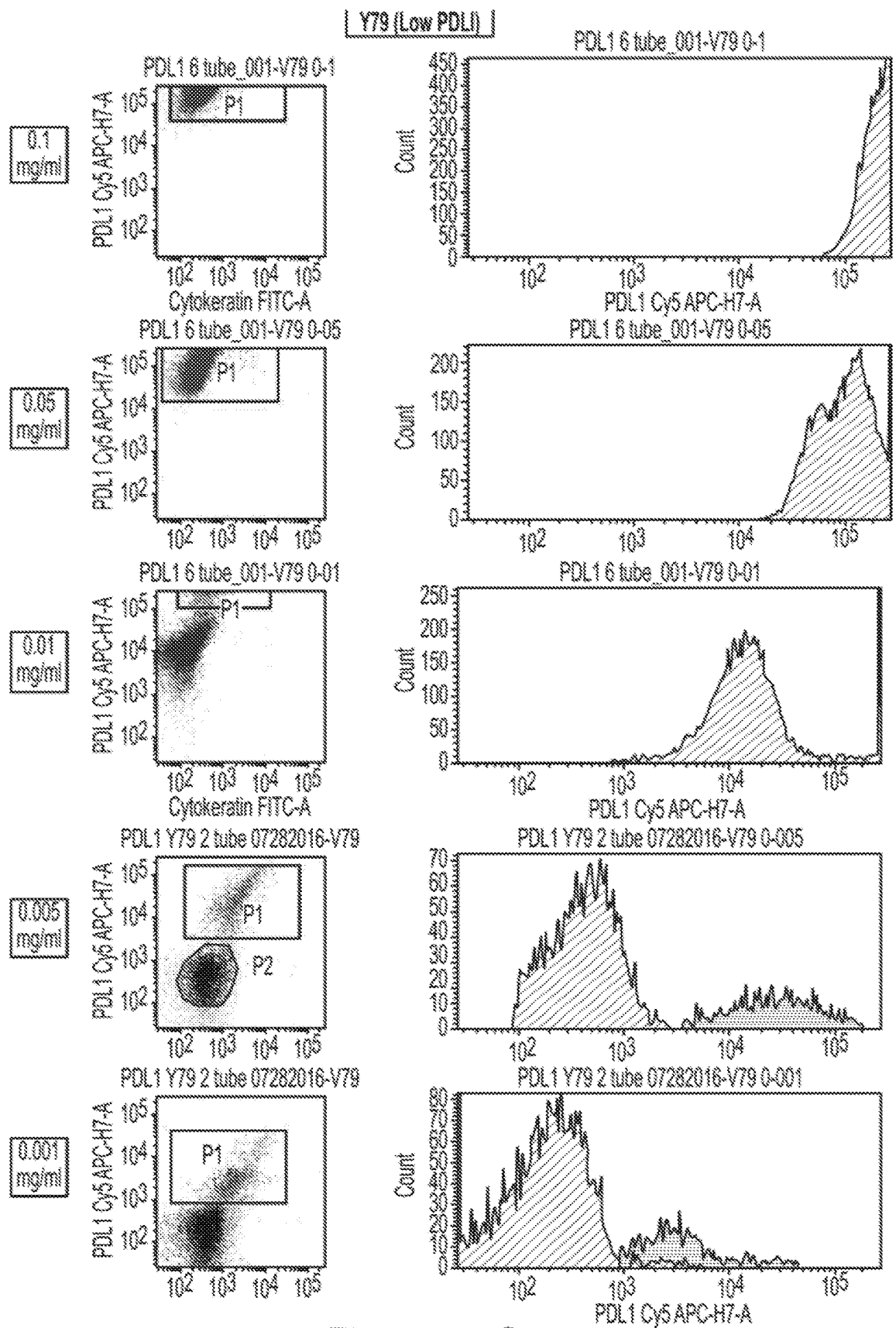
Figure 5:
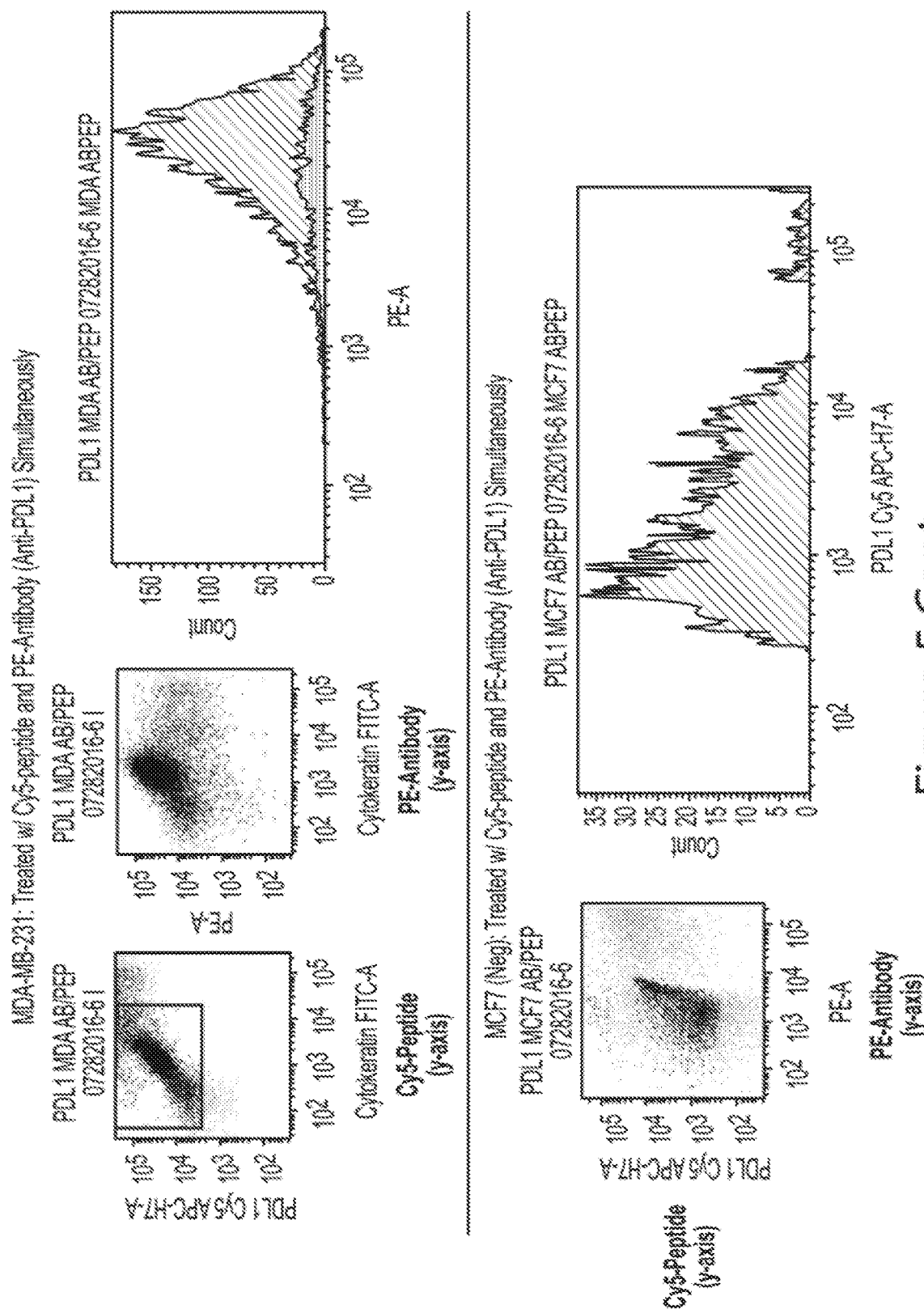
Figure 5:
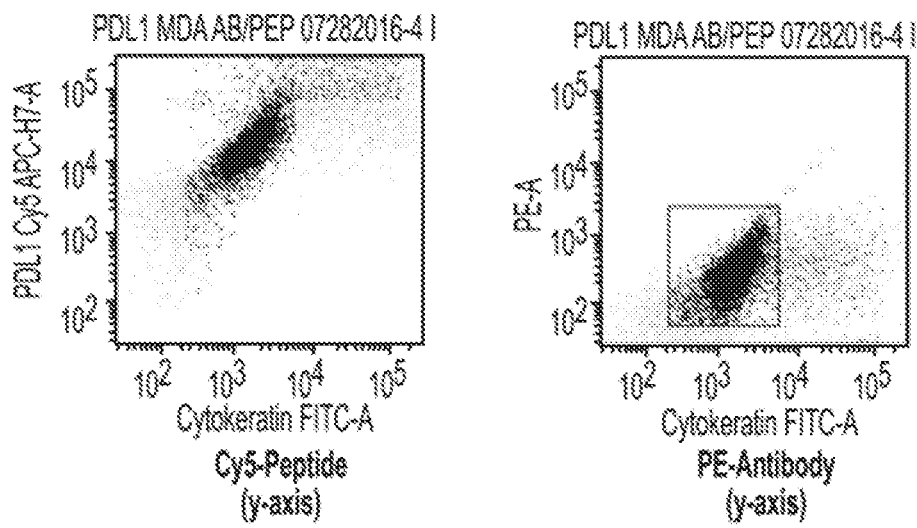
Figure 5:
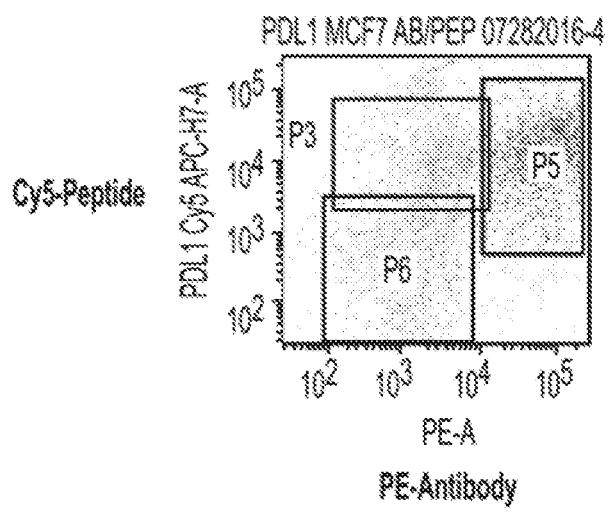

Blocking the interaction between Programmed Death Ligand 1 (PD-L1) and its receptor, PD-1, is an effective method of treating many types of cancers. Certain tumors overexpress PD-L1, causing host immune cells that express PD-1 to bind PD-L1 and cease killing the tumor. Inhibition of PD-L1 and PD-1 binding can restore host immunity towards tumor killing, and many new drugs have been developed to target this interaction. Current methods of PD-L1 diagnosis have shown to vary based on the antibody, detection kit brand, antigen retrieval method, and clinically defined methods by the FDA.

To refine detection of PD-L1, a synthetic ligand comprising a peptide or peptidomimetic compound (referred to generally herein as a "binding peptide") was invented to detect PD-L1 expressing tumors. In certain aspects, detection of a labeled ligand was achieved with immunohistochemistry (IHC) and/or flow cytometry. For example, in one aspect, flow cytometry was performed on cell lines and patient tissues using a fluorescently labeled peptide (RK-10-Cy5). For example, in another aspect, immunohistochemistry using a biotin-conjugated peptide (RK-10-Biotin) was tested against the FDA-approved SP263 clone on biopsied patient tissues. In this aspect, use of the RK-10 ligand showed staining in the tumor regions of FFPE tissues wherein use of SP263 did not. Also, in this aspect, the RK-10-Cy5 peptide demonstrated PD-L1 detection in NSCLC, breast, squamous cell carcinoma, and melanoma.

Definitions

The term "a" or "an" entity refers to one or more of that entity; for example, "a peptide" is understood to represent one or more peptides. As such, the terms "a" (or "an"), "one or more," and "at least one" can be used interchangeably herein.

It is understood that wherever aspects are described herein with the language "comprising," otherwise analogous aspects described in terms of "consisting of" and/or "consisting essentially of" are also provided.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. Numeric ranges are inclusive of the numbers defining the range. Even when not explicitly identified by "and any range in between," or the like, where a list of values is recited, e.g., 1, 2, 3, or 4, the disclosure specifically includes any range in between the values, e.g., 1 to 3, 1 to 4, 2 to 4, etc.

Units, prefixes, and symbols are denoted in their Système International de Unites (SI) accepted form. Unless otherwise indicated, amino acid sequences are written left to right in amino to carboxy orientation.

The headings provided herein are not limitations of the various aspects or aspects of the disclosure, which can be had by reference to the specification as a whole. The terms defined immediately below are more fully defined by reference to the specification in its entirety.

As used herein, the term "non-naturally occurring" substance, composition, entity, modification, and/or any combination of substances, compositions, entities, modifications, or any grammatical variants thereof, is a conditional term that explicitly excludes, but only excludes, those forms of the substance, composition, entity, modifications, and/or any combination of substances, compositions, entities, or modifications that are well-understood by persons of ordinary skill in the art as being "naturally-occurring," or that are, or might be at any time, determined or interpreted by a judge or an administrative or judicial body to be, "naturally-occurring."

As used herein, the term "peptide" is intended to encompass a singular "peptide" as well as plural "peptides," and refers to a molecule composed of monomers (amino acids) linearly linked by amide bonds (also known as peptide bonds). The term "peptide" refers to any chain or chains of two or more amino acids, and does not refer to a specific length of the product. Thus, dipeptides, tripeptides, oligopeptides, polypeptides, protein, amino acid chain, or any other term used to refer to a chain or chains of two or more amino acids are included within the definition of "peptide," and the term "peptide" can be used instead of, or interchangeably with any of these terms. The term "peptide" is also intended to refer to the products of post-expression modifications of the peptide, including without limitation glycosylation, acetylation, phosphorylation, amidation, derivatization by known protecting/blocking groups, proteolytic cleavage, or modification by non-standard amino acids. A peptide can be generated in any manner. A peptide can be made by chemical synthesis. A peptide can also be derived from a natural biological source or produced by recombinant technology, and can be, but is not necessarily, translated from a designated nucleic acid sequence.

As used herein, the term "peptidomimetic compound" and related "peptide mimetic," or just "peptidomimetic," and the like, which can be used interchangeably herein, is a molecule that mimics the biological activity of a peptide but is not strictly peptidic in chemical nature. For example, see U.S. Pat. No. 6,245,886, which is incorporated by reference herein. As taught in U.S. Pat. No. 6,245,886, in certain aspects, a peptidomimetic may not contain any peptide bonds. However, the term peptidomimetic is sometimes used to describe molecules that are not completely peptidic in nature, such as pseudo-peptides, semi-peptides and peptoids. Whether completely or partially non-peptidic in nature, for the purposes of this disclosure, peptidomimetics comprise a spatial arrangement of reactive chemical moieties that closely resembles the three-dimensional arrangement of sidechains on the peptide on which the peptidomimetic is based and have effects on biological systems that are similar to the biological activity of the peptide. Peptidomimetic compositions that correspond to or are equivalent to a PD-L1 binding peptide disclosed herein are capable of specifically binding to PD-L1.

By "specifically binds," it is meant that a binding molecule binds to PD-L1 with higher affinity than it would bind to a random, unrelated protein.

Detectably Labeled Ligand

This disclosure provides for detectably labeled synthetic ligands (also referred to as simply "ligand" or "ligands" herein) for detecting PD-L1. In certain aspects, the ligand specifically binds to PD-L1. In certain aspects, the ligand is detectably labeled to allow for detection of the ligand and in turn, such as when bound to PD-L1, detection of PD-L1. In certain aspects, the ligand comprises a standard amino acid peptide. In certain aspects, the ligand comprises a peptidomimetic compound as described elsewhere herein. One of ordinary skill would recognize that a peptide or a corresponding peptidomimetic compound has a sequence that is determined by the identity of the amino acid sidechains. In certain aspects, the peptide comprises the amino acid sequence SEQ ID NO: 1, which is an amino acid sequence that has been determined to bind to PD-L1. In certain aspects, the peptidomimetic compound comprises amino acid side chains following the entire sequential order of amino acid sequence SEQ ID NO: 1. SEQ ID NO: 1 is 19 amino acid residues in length. Thus, in certain aspects, the PD-L1-binding peptide portion of the ligand is 19 amino acids in length. It is contemplated that the peptide portion can be shorter than 19 amino acids, for example, the PD-L1-binding peptide portion of the ligand is 12, 13, 14, 15, 16, 17, or 18 amino acids in length, or any range or subrange in between and still specifically bind to PD-L1. The peptide portion can also be longer than 19 amino acids, for example, the PD-L1-binding peptide portion of the ligand is 20, 21, 22, 23, 24, 25, 26, 27, 28, 29, 30, 31, 32, 33, 34, 35, 36, 37, 38, or 39 amino acids in length, or any range or subrange in between and still specifically bind to PD-L1. In certain aspects, the PD-L1-binding peptidomimetic compound portion of the ligand is equivalent to 19 amino acids in length. It is contemplated that the peptidomimetic portion can be shorter than 19 amino acids, for example, the PD-L1-binding peptidomimetic portion of the ligand is equivalent to 12, 13, 14, 15, 16, 17, or 18 amino acids in length, or any range or subrange in between and still specifically bind to PD-L1. The peptidomimetic portion can also be longer than 19 amino acids in length, for example, the PD-L1-binding peptidomimetic portion of the ligand is equivalent to 20, 21, 22, 23, 24, 25, 26, 27, 28, 29, 30, 31, 32, 33, 34, 35, 36, 37, 38, or 39 amino acids in length, or any range or subrange in between and still specifically bind to PD-L1.

A ligand as disclosed herein can be detectably labeled by any of numerous methods known to one of ordinary skill in the art to detectably label a peptide or a peptidomimetic compound. For example, in certain aspects, the peptide or peptidomimetic compound can be labeled by direct incorporation of certain radioisotopes (e.g., radioisotopes of iodine (I) including $^{125}$I and $^{131}$I). In certain aspects, the peptide or a peptidomimetic compound can be labeled by the attachment, either directly or via a spacer (also sometimes referred to in the art as a "linker"), of a useful detectable label molecule (also referred to herein as simply a "detectable label") known to one of ordinary skill in the art. In certain aspects, the detectable label is a fluorescent molecule (e.g., a fluorophore), a non-fluorescent pigment or dye, a chelator for a radioisotope (including when associated with the radioisotope), an enzyme conjugate, or a heterologous epitope. Representative fluorescent molecules include but are not limited to: Alexa Fluor 350; Alexa Fluor 647; Oregon Green; Alexa Fluor 405; Alexa Fluor 680; Fluorescein (FITC); Alexa Fluor 488; Alexa Fluor 750; Cy3; Alexa Fluor 532; Pacific Blue; Pacific Orange; Alexa Fluor 546; Coumarin; Tetramethylrhodamine (TRITC); Alexa Fluor 555; BODIPY FL; Texas Red; Alexa Fluor 568; Pacific Green; Cy5; Alexa Fluor 594; a green, red, blue, yellow, etc. fluorescent protein. In certain aspects, the ligand is biotinylated, such as for use in the well-known avidin-biotin immunohistochemistry (IHC) detection system. In certain aspects, the detectable label is an enzyme such as horseradish peroxidase (HRP), alkaline phosphatase (AP), glucose oxidase, and β-galactosidase.

In certain aspects, the detectable label is attached directly to either the amine-end or the carboxy-end of the peptide or the equivalent end of the peptidomimetic compound. In certain aspects, the detectable label is attached directly to a sidechain of the peptide or peptidomimetic compound. In certain aspects, the detectable marker is attached to the peptide or peptidomimetic compound via a spacer. Numerous spacers are known to those of ordinary skill in the art including, but not limited to, non-peptide spacers such as polyethylene glycol (PEG) and amino acid or peptidomimetic spacers. In certain aspects, the spacer is an amino acid or peptidomimetic spacer. In certain aspects, the spacer comprises $(GS)_n$ or $(GGS)_n$, $(GGGS)_n$, or $(GGGGS)_n$, or peptidomimetic equivalent, wherein n is 1, 2, 3, 4, 5, 6, 7, 8, 9, or 10, or any integer range or subrange in between. In certain aspects, the spacer comprises $(GS)_n$, or a peptidomimetic equivalent, wherein n is 1 to 10, or wherein n is 3 to 5. In certain aspects, the spacer comprises $(GS)_3$, or a peptidomimetic equivalent. In certain aspects, the spacer consists of $(GS)_3$, or a peptidomimetic equivalent.

This disclosure provides for a ligand comprising a detectably labeled peptide of SEQ ID NO: 1 covalently attached at its amino end to a $(GS)_3$ amino acid spacer, designated herein as peptide RK-10 (SEQ ID NO: 2), or a peptidomimetic compound equivalent. In certain aspects, the detectably labeled ligand consists of a detectably labeled peptide covalently attached at its amino end to a $(GS)_3$ amino acid spacer, designated RK-10 (SEQ ID NO: 2), or a peptidomimetic compound equivalent. In certain aspects, the ligand is selected from the group consisting of the peptide ligand Biotin-$(GS)_3$—SEQ ID NO: 1 (RK-10-Biotin), the peptide ligand Cy5-$(GS)_3$-SEQ ID NO: 1 (RK-10-Cy5), and peptidomimetic compound ligands corresponding to either. These same ligands can also be represented by reference to SEQ ID NO: 2, i.e., the peptide ligand Biotin—SEQ ID NO: 2 (RK-10-Biotin) or the peptide ligand Cy5—SEQ ID NO: 2 (RK-10-Cy5).

This disclosure provides for a composition comprising a ligand as disclosed herein. In certain aspects, the composition comprises a compound that stabilizes the ligand, either in sample and/or in a subject. In certain aspects, the composition comprises a pharmaceutically acceptable excipient.

PD-L1 Detection

The disclosure provides for methods of detecting PD-L1 in a sample. In certain aspects, the method comprises contacting a detectably labeled ligand or composition comprising a ligand disclosed herein with a sample. One of ordinary skill in the art will understand from well-known detection methods and/or the non-limiting illustrative examples provided herein, permissive conditions that will allow the ligand to specifically bind to PD-L1. In certain aspects, the sample is additionally washed or otherwise treated to clear and remove unbound and excess ligand. The sample can be any sample for which detection of the presence of PD-L1 is desired. For example, the sample can be a biological tissue or cells from a subject or a component or components isolated, purified, or otherwise derived from such tissue or cells. Representative examples include blood and/or tumor tissue from a cancer patient. In certain aspects, the cancer is lung (e.g., NSCLC), breast, squamous cell carcinoma, melanoma, prostate, or colorectal cancer. In certain aspects, the subject can be a human or a non-human (e.g. animal) such as a non-human primate, companion animal such as a cat or dog, or livestock or other domesticated animal. In certain aspects, the sample is used as a control, such as a control tissue or control cells, know to either express or known not to express PD-L1 and/or a sample comprising isolated, purified, or manufactured PD-L1. In certain aspects, the sample is a human or animal cancer cell line or placenta. Representative examples of PD-L1 expressing cell lines include A549, T47D, SKBR-23, and MCF-7.

In certain aspects, the sample is fixed to a substrate such as a specimen slide, a multi-well plate, or an array such as a microarray. In certain aspects, the sample is dissociated, such as suspended cells, as can be sorted and/or analyzed using flow cytometry.

Following contact of the sample with the detectably labeled ligand and optionally clearing of unbound ligand, the sample is assayed for the presence of the ligand. Based on the type of detectable label utilized, the appropriate assay method for detecting the ligand would be understood by one of ordinary skill in the art. For example, the presence of a fluorescently labeled ligand can be detected by illumination with light of a particular wavelength and observation at the wavelength emitted, the presence of a biotin labeled ligand can be detected using IHC techniques, and the presence of an enzyme conjugate can be detected by reaction with the enzyme substrate. In certain aspects, the presence of the ligand can be detected using flow cytometry, a method which can also sort cells and/or provide information about the presence of the ligand within a population of cells.

In certain aspects, the presence of the ligand is indicative of the amount of PD-L1 in the sample and/or the subject from which the sample was obtained. In certain aspects, the amount of PD-L1 detected as determined by detection of the ligand can be compared against a predetermined standard or against a different sample. In certain aspects, a subject can be diagnosed, such as having or not having cancer, based on the amount and/or other feature(s), such as localization, of PD-L1 detected. In certain aspects, the cancer is lung (e.g., NSCLC), breast, squamous cell carcinoma, melanoma, prostate, or colorectal cancer. In certain aspects, treatment of the cancer is based on the detection of PD-L1 in a subject sample by the detectably labeled ligand disclosed herein. In certain aspects, treatment of a subject having cancer is based on comparison of PD-L1 in a subject sample with a predetermined standard.

This disclosure provides for detecting PD-L1 in a subject. In certain aspects, the method comprises administering the a detectably labeled ligand or composition comprising a ligand disclosed herein to a subject. Following administration, the presence of the labeled ligand in the subject is assayed. Based on the type of detectable label utilized, the appropriate assay method to detect the ligand would be understood by one of ordinary skill in the art. For example, certain nuclear medicine isotopes can be imaged by positron emission tomography (PET) scan. Thus, in certain aspects, the location of the labeled ligand in the subject is visualized. In certain aspects, the location of PD-L1 expression is indicative of the location of cancer cells and/or tumors. In certain aspects, the method comprises treating a subject's cancer based on the location of the tumor as detected by visualization of the ligand.

Method of Manufacture

This disclosure provides for methods of making a detectably labeled synthetic ligand as disclosed herein for detecting PD-L1. In certain aspects, the method comprises incorporating a detectable label into, or attaching either directly or via a spacer a detectable label to, a peptide or peptidomimetic compound that comprises amino acid sidechains following the entire sequential order of the amino acid sequence SEQ ID NO: 1, as described herein. In certain aspects, the detectable label is any of the aforementioned labels.

For example, in certain aspects, an amino acid spacer is attached to either the amino end or carboxy end of a peptide of SEQ ID NO: 1 or an equivalent peptidomimetic compound. In certain aspects the amino acid spacer (such as a $(GS)_3$ spacer) is covalently attached to the amino end of the peptide or peptidomimetic compound. In certain aspects, a detectable label is attached to the peptide or peptidomimetic compound via the spacer.

This disclosure provides for methods of making a detectably labeled synthetic ligand as disclosed herein for detecting PD-L1. In certain aspects, the labeled ligand comprises a peptide or peptidomimetic compound that comprises amino acid sidechains following the entire sequential order of the amino acid sequence SEQ ID NO: 1 as described herein and the method comprises synthesizing the peptide or peptidomimetic compound.

PD-L1 Binding Peptide and Peptidomimetic Compound

This disclosure provides for an isolated peptide comprising the amino acid sequence SEQ ID NO: 1, wherein the peptide is from 19 to 39 amino acids in length as described herein and wherein the peptide comprises at least one non-naturally occurring modification. In certain aspects, the modification is the incorporation of attachment of a detectable label that allows for detection of the peptide. In certain aspects, the modification is one that increases the stability, such as increasing the half-life of a ligand comprising the peptide in a blood sample or when administered to a subject. In certain aspects, the modification increases binding to PD-L1 or increases biofouling.

This disclosure also provides for a peptidomimetic compound comprising amino acid sidechains following the entire sequential order of the amino acid sequence SEQ ID NO: 1 wherein the peptidomimetic compound has a length equivalent to 19 to 39 amino acid residues as described herein. A peptidomimetic compound corresponding to a peptide, rather than the peptide itself, may be used to improve bioavailability, duration of action, stability, storage, and immunoreactivity. The techniques of developing peptidomimetics are conventional. For example, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure.

Kits

This disclosure provides for a kit for detecting PD-L1 comprising a peptide or peptidomimetic compound as disclosed herein. In certain aspects, the peptide or peptidomimetic compound in the kit is detectably labeled or the kit provides reagents and/or instructions for labeling the peptide or peptidomimetic compound. For example, in certain aspects, the kit contains a detectably labeled synthetic ligand provided herein. In certain aspects, the kit also comprises reagents and/or instructions for detecting the detectably labeled peptide or peptidomimetic compound or ligand. In certain aspects, the kit comprises a pharmaceutically acceptable excipient for combination with the peptide or peptidomimetic compound to form a composition.

EXAMPLES

Materials and Methods

All experimental protocols under Evaluation of Molecular Mutations in Lung Cancer, IRB #2004603, were approved by the University of Missouri Institutional Review Board. All methods were carried out in accordance with relevant guidelines and regulations. All patient specimens were obtained from the tissue core and the samples were collected previously with informed consent.

Identification of RK-10 Peptide.

The RCSB protein data bank was searched for the complex of PD1 and PD-L1. Out of the results, the structure corresponding to the PDB ID "4ZQK" was selected for analysis because it represents the Structure of the complex of human programmed death-1 (PD-1) and its ligand PD-L1 in its non-mutated form with an X-ray resolution of 2.45 Å. The selected structure was visually examined using the open-source program PyMOL Molecular Graphics System Version 1.8.20. A proprietary Fortran program was developed and used to analyze interactions between residues within the binding region. If distance between two residues in the binding region was less than or equal to 1.2 times the sum of the Van der Waal's radii of the two atoms, it was regarded to be a contact and the residue-residue contact count was updated to +1. Number of occurrences for each sequence was calculated and used to identify the peptide sequences used in this study.

Flow Cytometry Using Cultured Cell Lines.

Cell lines MDA-MB-231, Y79, and MCF-7 were purchased from ATCC, thawed, and grown in culture to confluency. When confluent, adherent cells were removed from the flask by scraping gently with a cell scraper and media removed using centrifugation. Suspension cells were pipetted from the flask and centrifuged to remove media. Cell lines were resuspended in Eppendorf tubes in 100 μL PBS at a concentration of $5 \times 10^6$ cells per mL. Cy5-conjugated peptide solution was then added to the tubes to make the desired concentration of peptide in 200 μL. Eppendorf tubes were then placed in the incubator for 1 hour and vortexed at the 30-minute mark. After 1 hour, cell lines were analyzed on a BD FACS Canto II, a 3-laser, 8-color flow cytometer (San Jose, Calif.) using Diva 8.0 acquisition and analysis software (San Jose, Calif.). The cells of interest were gated using Forward and Side scatter (FSC/SSC) and positive antibody expression. 10,000 singlet events were collected for each specimen.

Flow Cytometry Using Tissues.

Cases were evaluated using flow cytometry for suspected hematopoietic neoplasms. A portion of each fresh specimen was collected into RPMI. Each sample was prepared to create cell suspensions which were combined with neat amounts of the following antibodies (BD, San Jose, Calif.): CD15 FITC, CD34 PE, CD33 PerCP-Cy5-5, CD13 PE-Cy7, CD11B APC, HLA-DR APC-H7, CD16 V450, CD45 V500C, Kappa FITC, Lambda PE, CD5 PerCP-Cy5-5, CD19 PE-Cy7, CD23 APC, CD20 APC-H7, CD10 BV421 V450, CD4 FITC, CD8 PE, CD2 PE-Cy7, CD56 APC, CD3 APC-H7, CD7 V450, CD38 PerCP-Cy5-5, CD10 APC, CD5 BV421 V450, CD23 PE, CD8 PE-Cy7, CD200 APC, and CD138 PerCP-Cy5-5 (Dako, Carpinteria, Calif.) and incubated for 15 minutes in the dark. Any erythrocytes within the specimens were lysed with BD PharmLyse (San Jose, Calif.) and the specimens were washed with BD Staining Buffer with BSA (San Jose, Calif.). Each sample was evaluated using BD FACSCanto II, a three laser, eight-color flow cytometer (San Jose, Calif.) within 24 hours of collection. 50,000 events were collected for each sample. The expression data were analyzed using BD FACSDiva software, version 8.0 (San Jose, Calif.). Cases diagnosed as non-hematopoietic tumors were further subjected to evaluation with PDL-1 peptide if material was available combined with CK to identify the epithelial component. The cell suspensions were stained with 10 μl of BD Cytokeratin FITC (clone CAM5.2), 20 μl of Cy5-conjugated peptide solution, and 10 μl of BD Pharmingen CD274 PE (clone MIH1), incubated in the dark for 30 minutes, washed with BD Stain Buffer with BSA, and reconstituted to 500 μl with Stain Buffer with BSA in 500 ml polystyrene tubes for analysis. The specimens were analyzed on the FACS Canto II using the same panel template, gating strategy, and collection events as the cell line specimens.

Immunohistochemistry Using Biotinylated Peptide.

To detect PD-L1 in FFPE tissues, manual IHC techniques were employed with a biotin-conjugated version of peptide RK-10-Cy5 and compared with Ventana PD-L1 (SP263) Rabbit monoclonal Primary Antibody stained on a Roche Benchmark Ultra autostainer. Seven PD-L1 expressing NSCLC patient tissues were obtained from the MU One-Health tissue bank and de-identified according to IRB protocols. Paraffin-embedded patient tissue slides were baked overnight, then de-waxed and rehydrated according to standard protocols. Tissue sections were then subjected to antigen retrieval in EDTA at 95° C. for 20 minutes in EDTA (pH 0.9). The solution is then cooled for an additional 20 minutes on the bench top prior to buffer rinse. Tissues were then incubated with 15 biotinylated peptide for 2 hours in a humid chamber at RT. After 2 hours, slides were washed with buffer and treated with PIERCE™ High Sensitivity Streptavidin-HRP (1:200 dilution) (Sigma) for 30 minutes at RT in a humid chamber. Once this was complete, slides were again washed in buffer then treated with DAB (3,3'-Diaminobenzidine; Sigma) for 10 minutes. Slides were again washed in buffer, then dehydrated using graded alcohol and xylene and counterstained with hematoxylin. Slides were then imaged using bright-field microscopy on a Leica DM5500.

Immunohistochemistry Using Cy5-Peptide.

PD-L1 expression was investigated in the same seven FFPE tissues and 192 lung cancer cases on a microarray using our peptide conjugated with Cy5 fluorophore. A lung cancer tissue microarray (TMA) was purchased from U.S. Biomax that contains 192 separate cases of various types of lung cancers (LC1923, biomax.us). In addition, seven NSCLC patient tissues were obtained from the Mizzou OneHealth tissue bank and de-identified according to IRB protocols. Paraffin-embedded tissue slides were baked overnight, then de-waxed and rehydrated according to standard protocols. Tissue sections were then subjected to antigen retrieval in EDTA at 95° C. for 20 minutes in EDTA (pH 0.9). The solution was cooled for an additional 20 minutes on the bench top prior to buffer rinse. Tissues were then incubated with 15 µM Cy5-conjugated peptide for 2 hours in a humid chamber in the dark at RT. After 2 hours, slides were washed with buffer. The slides were then mounted using nucleus-specific DAPI counterstain and cover slipped. Slides were then imaged using fluorescence microscopy on a Leica DM5500 and compared to the same sections which had been stained with the Ventana antibody. For fluorescent analysis, DAPI channels and Cy5 channels were overlaid to image cell nuclei and PD-L1 expression, respectively.

IHC Blocking Using PD-L1 Peptide or Ventana Antibody SP263.

To test specificity of the PD-L1 peptide, PD-L1 receptors were first blocked on the tissue with RK-10 peptide for 1 hour prior to autostaining the tissue with SP263 antibody using the Roche autostainer with the Ventana PD-L1 kit according to Roche's specifications. Blocking of the RK-10 peptide using the SP263 antibody was also investigated by first treating the tissue with SP263 antibody for 30 minutes prior to treating the tissue with peptide according to the previously mentioned protocol.

Results

Identification of PD-L1 Binding Peptide and Mock Peptide.

Figure 14:
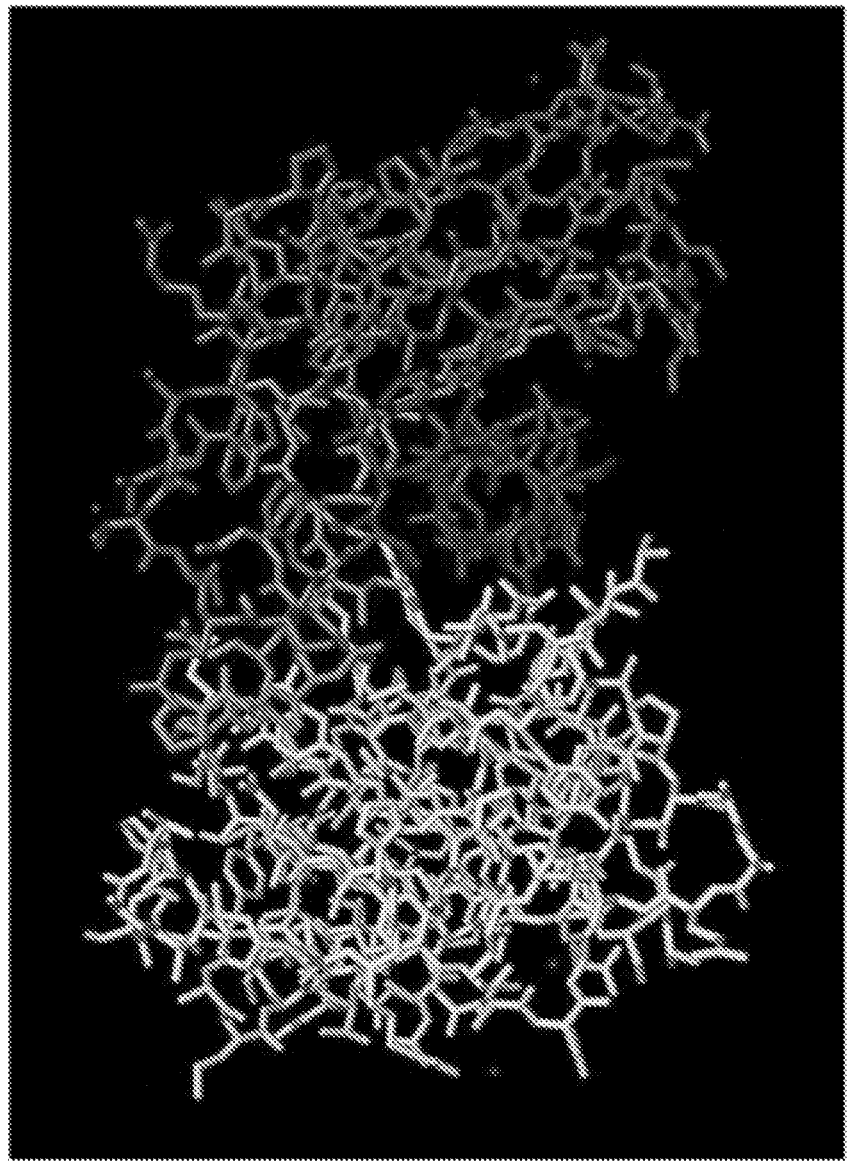
FIG. 14 shows interactions of PD-1 and PD-L1 based on X-ray crystal structure data.

Initial research was focuses on understanding the interaction of PD-1 and PD-L1 based on X-ray crystal structure data (FIG. 14) with the goal of identifying the peptide sequence that is selectively mediating the interactions. After the crystal structure of each protein was identified, a proprietary Fortran program was used to analyze which amino acid sequences interact most closely between the two proteins. Number of occurrences for each sequence was calculated and used to identify the peptide sequences used in this study. The calculations provided several sequences of peptide that could possess high-affinity for targeting PD-L1 in tumor. As a first step, a library of peptides was synthesized and the stability and PD-L1 affinity was studied. The study resulted in identification of a high affinity peptide, RK-10-Cy5 for targeting PD-L1. Data related to anti-PD-L1 and mock peptide was used to synthesize peptides for this study. The binding sequences of each peptide were further modified to incorporate either biotin or fluorophore for antigen detection, and to increase solubility of the peptide.

Fluorescent RK-10-Cy5 as Marker for Flow Cytometry.

Figure 6A:
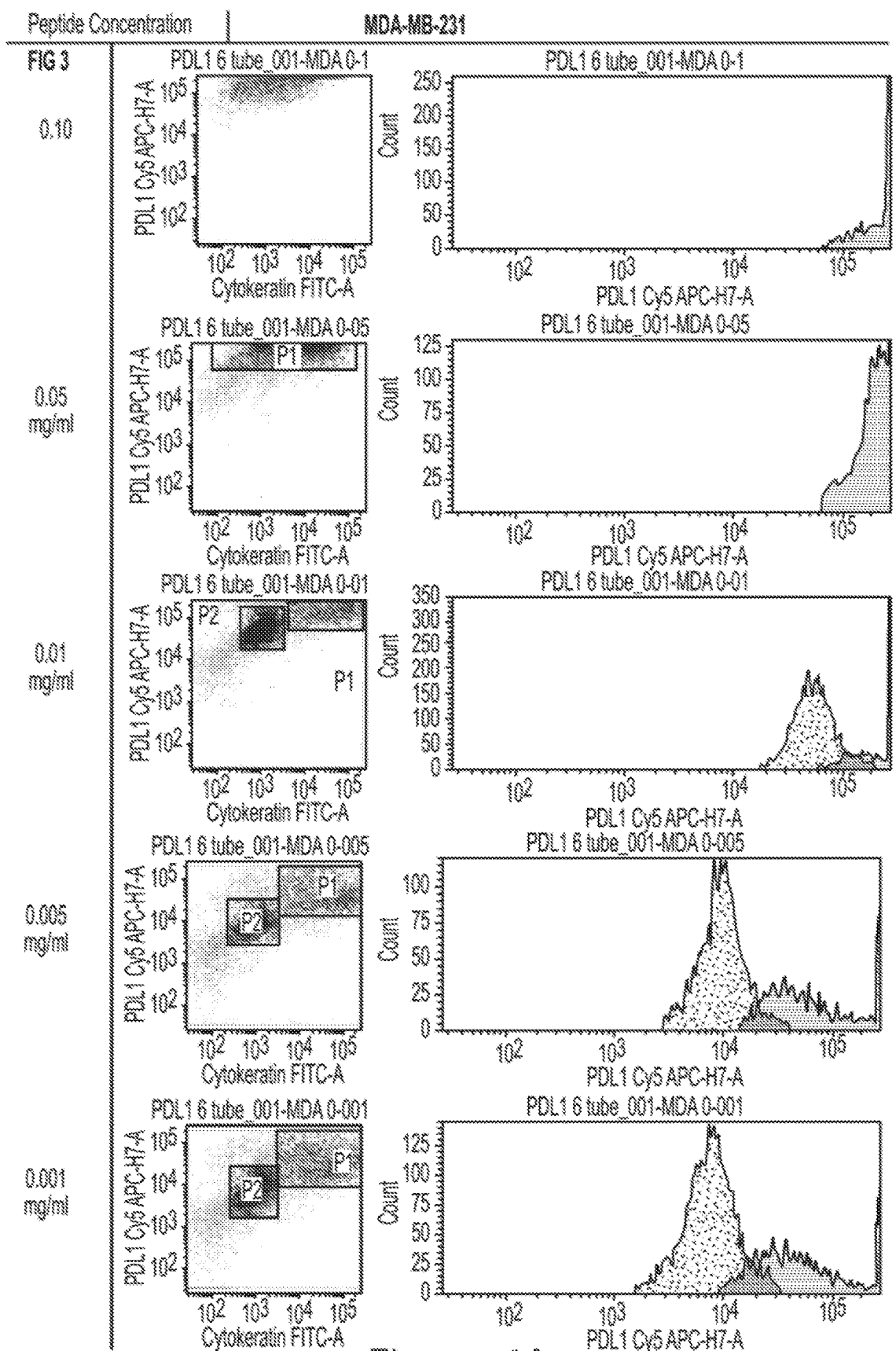
FIG. 6A shows representative flow cytometry analysis of PD-L1 expression in cell lines.
Figure 6A:
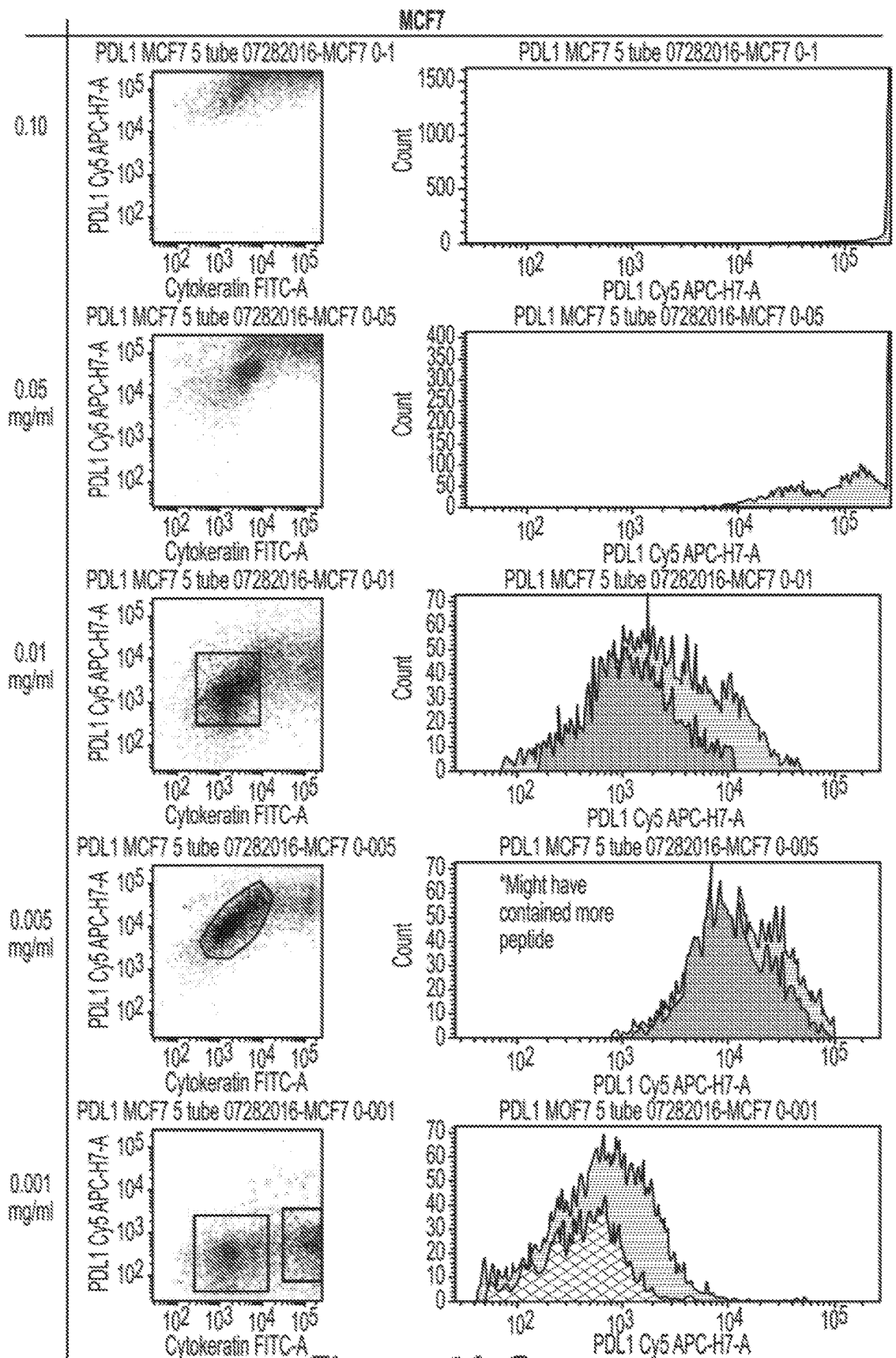
Figure 6A:
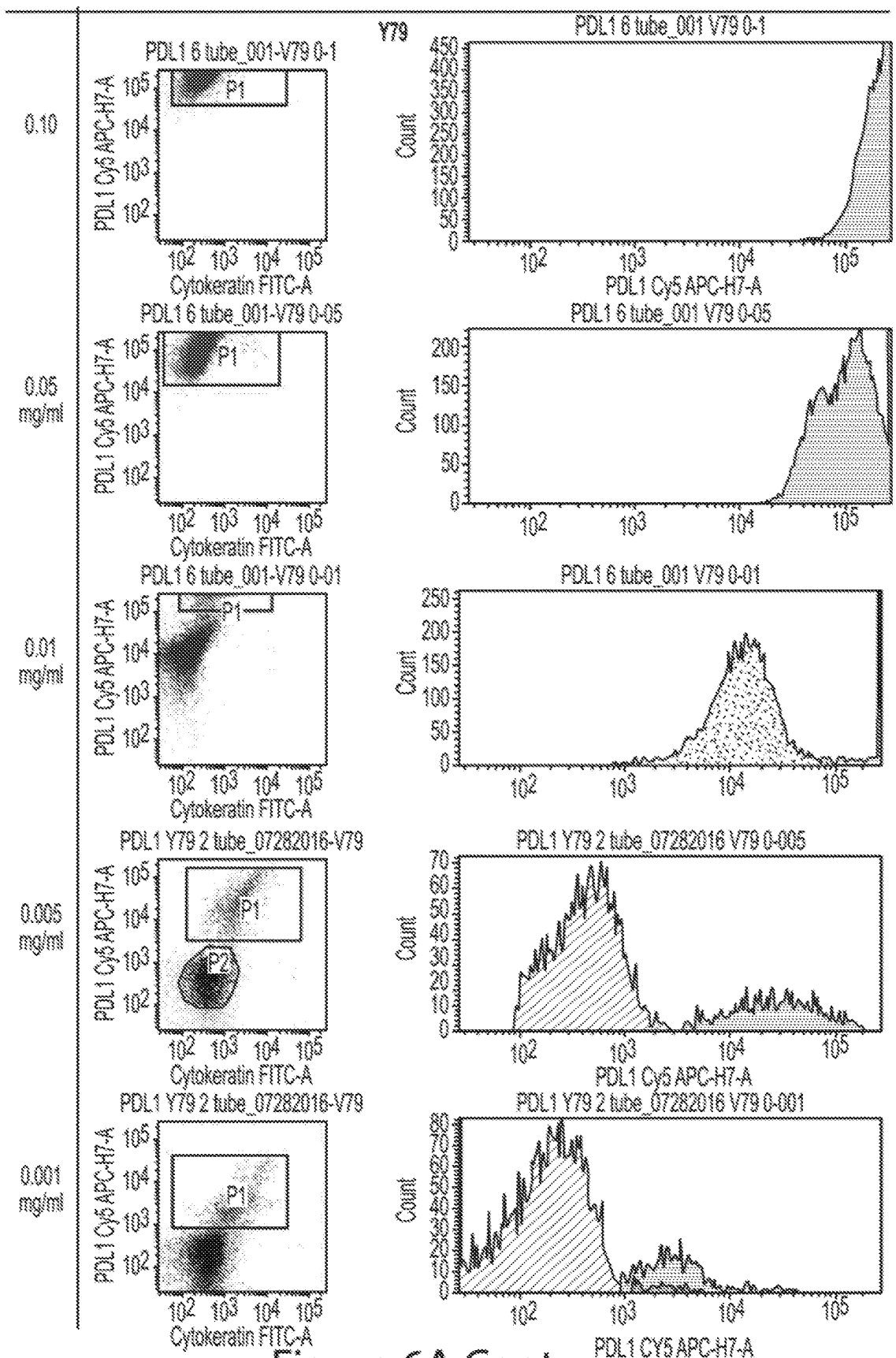
Figure 6B:
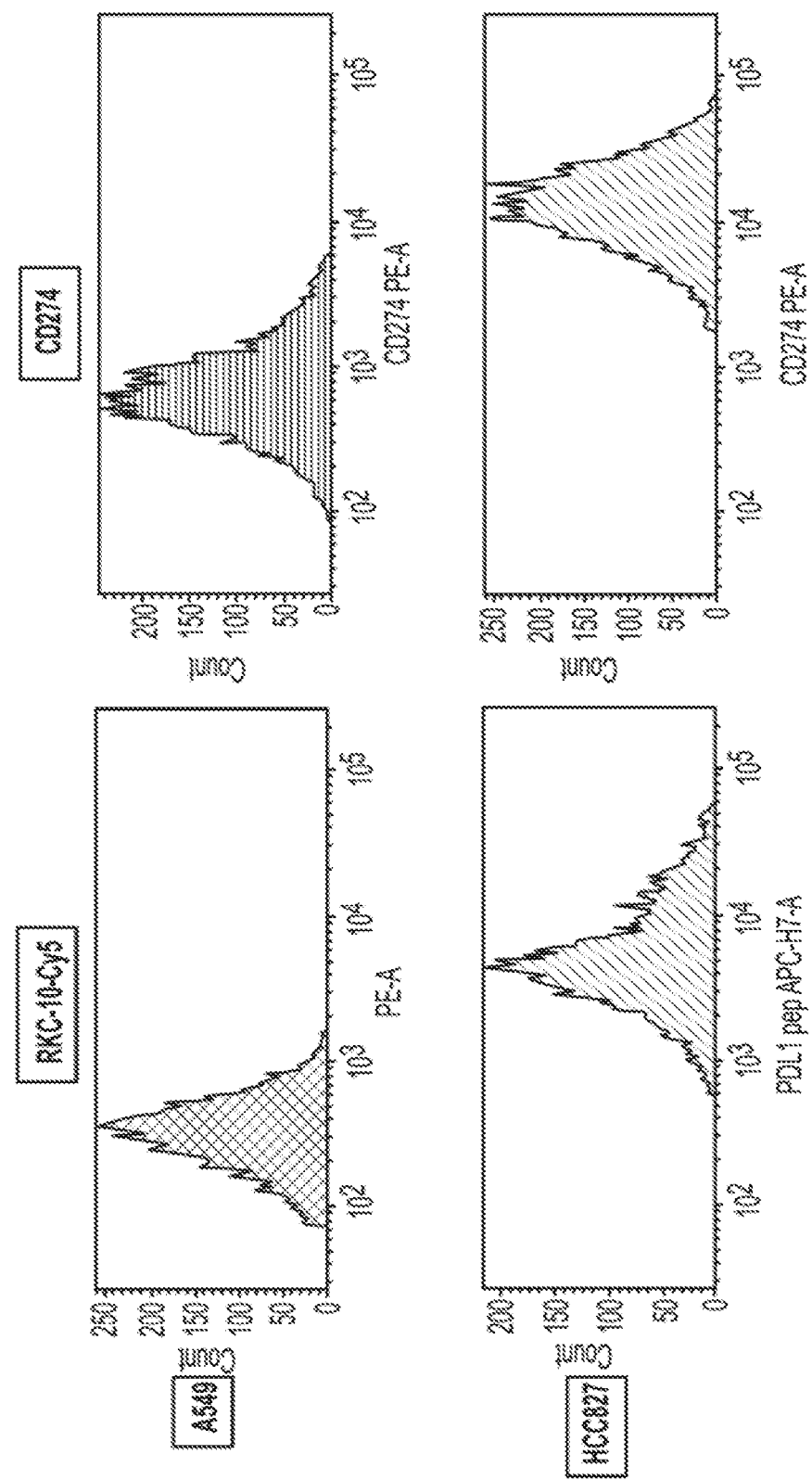
FIG. 6B shows representative flow cytometry analysis of PD-L1 expression in cell lines.
Figure 15:
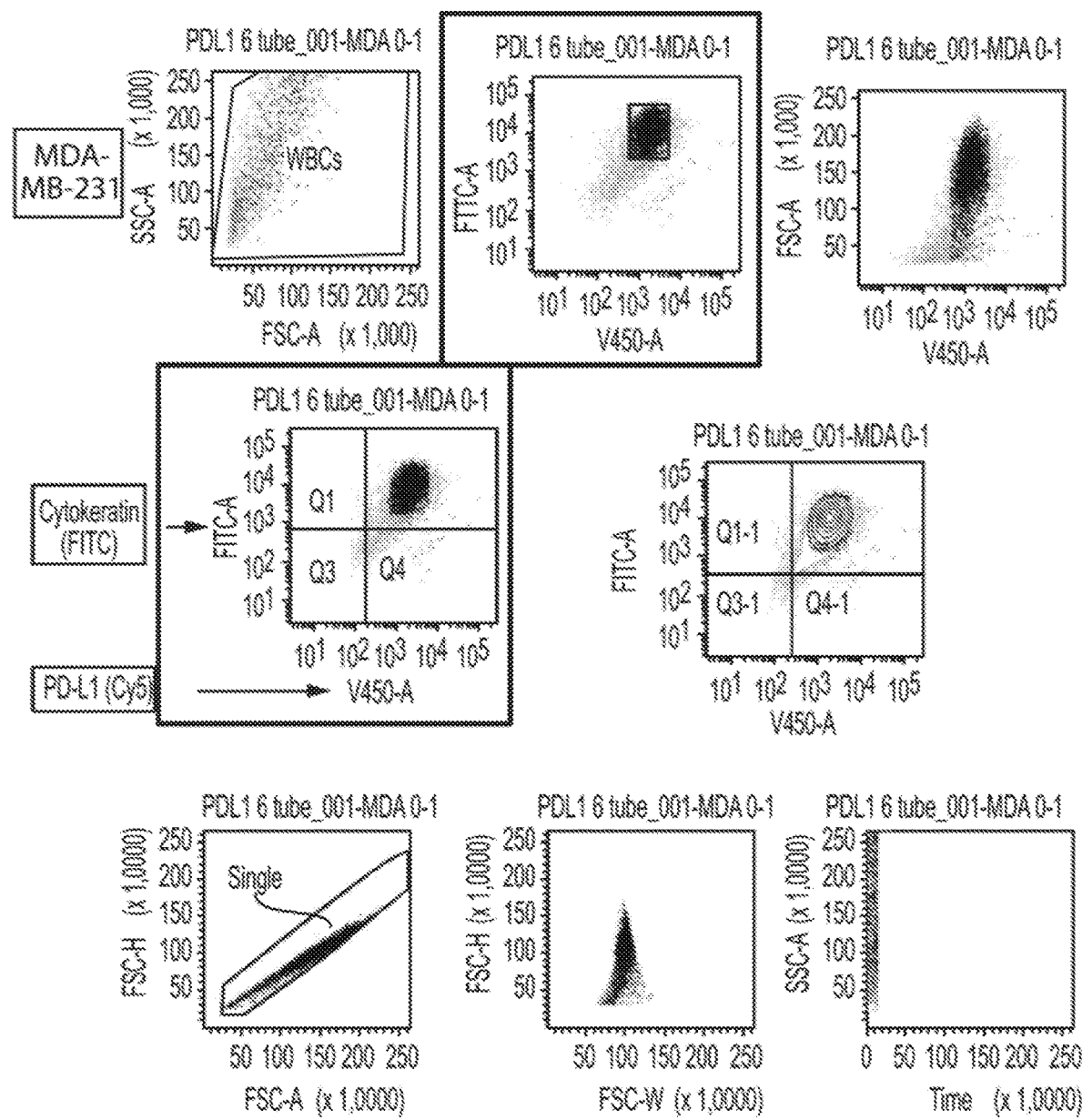
FIG. 15 shows analysis of PD-L1 expression of both cytokeratin (FITC channel) and PD-L1 (Cy5 channel).

RK-10-Cy5 was then investigated for PD-L1 specificity using flow cytometry in cultured cell lines and patient tissues. The cell lines examined were breast cancer line MDA-MB-231, which shows very high PD-L1 expression, along with retinoblastoma line Y79 and breast cancer line MCF-7, which show no meaningful PD-L1 expression. To set our conditions for flow cytometry, titrations of PD-L1 peptide using all three cell lines were first examined. In each of the samples double-positives were selected by analyzing expression of both cytokeratin (FITC channel) and PD-L1 (Cy5 channel) (FIG. 15). All three cell lines showed a decrease in mean fluorescence intensity (MFI) as the concentration of peptide decreased (FIG. 6A). Samples containing 0.1 and 0.05 mg/mL concentrations were deemed to have fluorescence intensities too high for accurate analysis for each cell line. Y79 and MCF7 both have a much lower PD-L1 expression than MDA-MB-231, which correlates with expression seen using Cy5 conjugated peptide and comparing the cell lines with flow cytometry. Y79 and MCF7 MFI is close to tenfold lower than that seen in MDA-MB-231 in all lower concentrations. The MCF7 sample containing 0.005 mg/ml was much higher than anticipated due to this sample being treated twice with peptide. 0.005 mg/mL was selected as optimal concentration based on these comparisons, and all subsequent flow cytometry experiments were performed using this concentration. Lung cancer cell lines A549 (low PD-L1) and HCC827 (high PD-L1) were investigated for PD-L1 expression using both phycoerythrin-conjugated cd274 and RK-10-Cy5 (FIG. 6B). Cell lines were cultured as before and treated with either antibody or peptide in buffer. When run through the flow cytometer, a much higher signal was observed associated with PD-L1 expression in the HCC827 cell line than in the A549 samples. The antibody associated fluorescence was higher than the peptide associated fluorescence in both samples, which is attributed to differences in titrating peptide and antibody.

Detection of PD-L1 in Circulating Tumor Cells and Patient Tissues.

Whole blood samples were spiked with MDA-MB-231 cells to see if detection of low cell counts in blood samples, such as circulating cells, could be achieved using RK-10. MDA-MB-231 were diluted with whole blood, then treated with RK-10 and cytokeratin before staining. These samples were also treated with a PE-conjugated antibody CD274 (BD Pharmingen) against PD-L1 to further verify PD-L1 detection. Positive signals of cytokeratin and PD-L1 expression at low counts in the whole blood sample using both the peptide and the antibody were able to be detected.

Lung cancer cell lines A549 (low PD-L1) and HCC827 (high PD-L1) were investigated for PD-L1 expression using both cd274 and RK-10. Cell lines were cultured as before and treated with either antibody or peptide in buffer. When run through the flow cytometer, a much higher signal associated with PD-L1 expression in the HCC827 cell line than in the A549 samples was observed. The antibody associated fluorescence was higher than the peptide associated fluorescence in both samples, which is attributed to differences in titrating peptide and antibody.

Figure 7A:
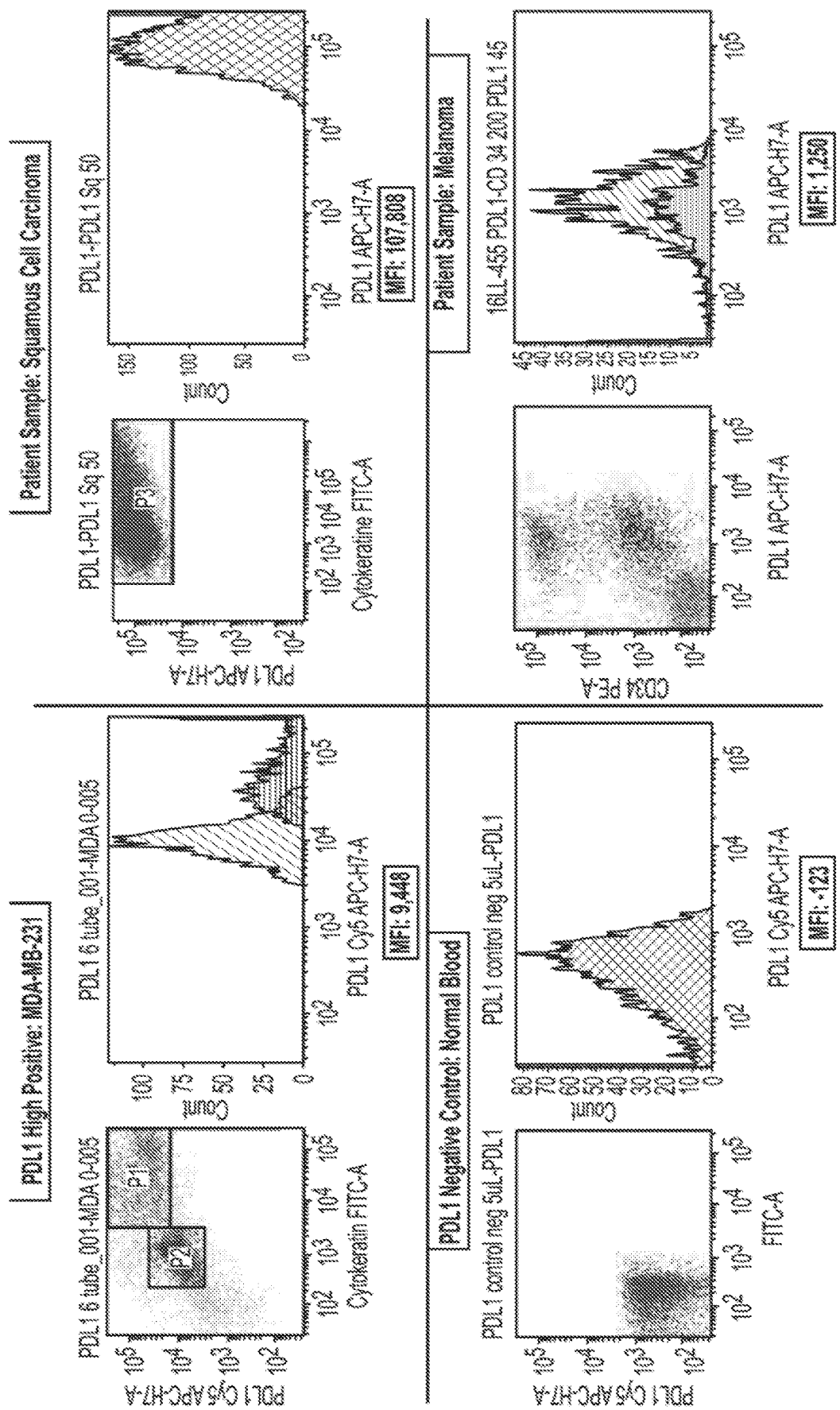
FIG. 7A shows representative flow cytometry analysis of PD-L1 expression in samples obtained from a subject.
Figure 7B:
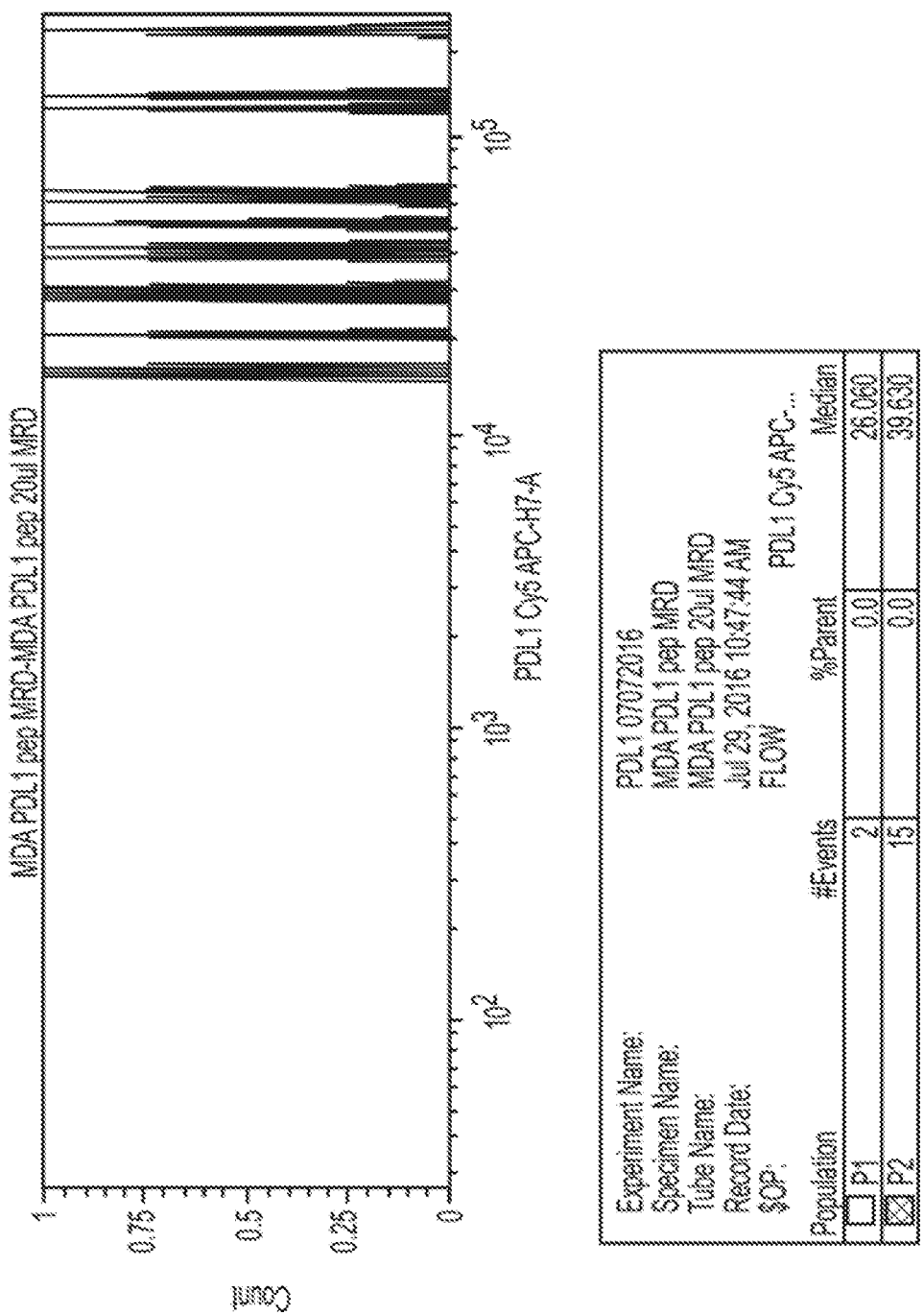
FIG. 7B shows representative flow cytometry analysis of PD-L1 expression in samples obtained from a subject.

PD-L1 expression in patient tissues was analyzed using RK-10-Cy5 and compared to expression in MDA-MB-231 cells and a negative control of normal blood (FIG. 7A). The MFI of the MDA-MB-231 cells was 9,448, while the whole blood gave an MFI of −123. Squamous cell carcinoma and metastatic melanoma samples were investigated for PD-L1 expression using the previously mentioned MFIs as high and negative, respectively. The squamous cell carcinoma was shown as having an MFI of 107,808, while the melanoma sample gave an MFI of 1,250. The squamous cell carcinoma PD-L1 expression was very high, while the melanoma sample was graded as 'moderate' PD-L1 expression, and additionally showed no expression of cytokeratin. Since loss of CK expression is consistent with circulating tumor cells, it was thought that RK-10-Cy5 peptide could be used to detect CTCs. To see whether detection of low cell counts was possible, whole blood samples were spiked with MDA-MB-231 cells. MDA-MB-231 were diluted with whole blood, then treated with RK-10-Cy5 and cytokeratin before staining. These samples were also treated with a phycoerythrin-conjugated antibody (cd274) against PD-L1 to further verify PD-L1 detection. Positive signals were detected of cytokeratin and PD-L1 expression at low counts of ~15 cells in 1 mL whole blood sample using both the peptide and the antibody (FIG. 7B).

Biotinylated RK-10-Biotin Detects PD-L1 in NSCLC Patient Tissues.

Figure 8:
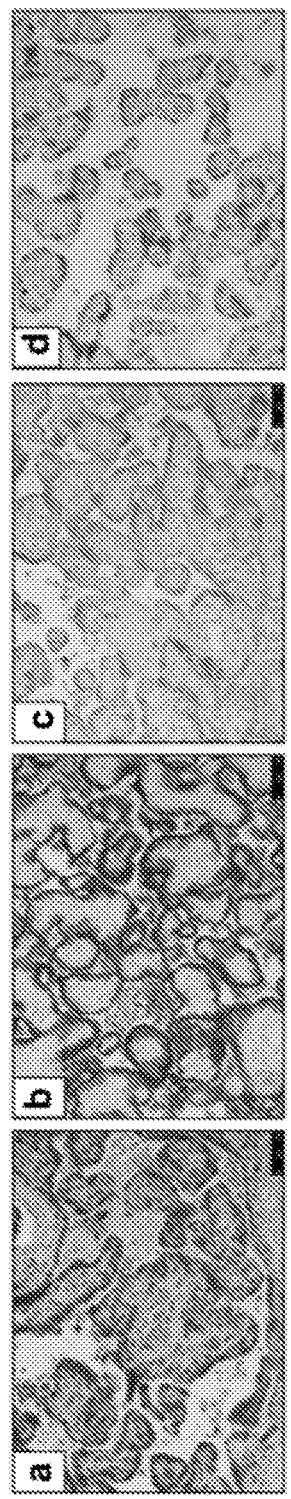
FIG. 8 shows placental tissue staining with the PD-L1 binding peptide.

Seven Patient NSCLC tissues were investigated for PD-L1 using either manual IHC with 15 μM RK-10-Biotin peptide, or the Ventana PD-L1 (SP263) rabbit monoclonal primary antibody stained on a Roche Benchmark Ultra. In this study the peptide was conjugated with biotin, which was used to bind a secondary treatment of streptavidin-HRP. Formalin-Fixed, Paraffin Embedded (FFPE) placenta tissue was used as the positive control, since PD-L1 is expressed in placental trophoblasts (Veras, E., Kurman, R. J., Wang, T.-L. & Shih, I.-M. *International Journal of Gynecological Pathology* Publish Ahead of Print). This study also utilized biotinylated mock peptide RK-11-Biotin as a negative control. This mock peptide was synthesized to have very low affinity to PD-L1. Both the PD-L1 peptide and Ventana clone SP263 stained the trophoblasts heavily in the placental tissue (FIG. 8). The SP263 antibody featured heavy edge staining but also showed membranous staining of the trophoblast cells, while the RK-10-Biotin peptide showed heavy membrane staining of the trophoblast cells without the intense edge artifacts seen when using the Ventana antibody. Mock peptide RK-11-Biotin showed light staining at high concentrations, but did not achieve the heavy trophoblast staining RK-10-Biotin did. Higher concentrations of RK-10 peptide showed more staining in other parts of the placental tissue, but the heaviest staining is localized to the trophoblast cells. Blocking of the Ventana antibody was achieved by first treating the placenta tissue with RK-10-Biotin for 30 minutes, washing, and treating on the Roche autostainer according to specifications. The pre-blocked tissue showed drastic reduction of staining, with mostly edge artifacts being seen (FIG. 8, panel c). Placenta tissue that was not pre-blocked was stained with the Ventana kit in parallel with the pre-blocked tissue, and showed the expected trophoblast staining as before. As a negative control, normal lung, breast, and colorectal tissues were stained using RK-10 and SP263. Each of these cases were determined as negative for PD-L1 expression.

Figure 9:
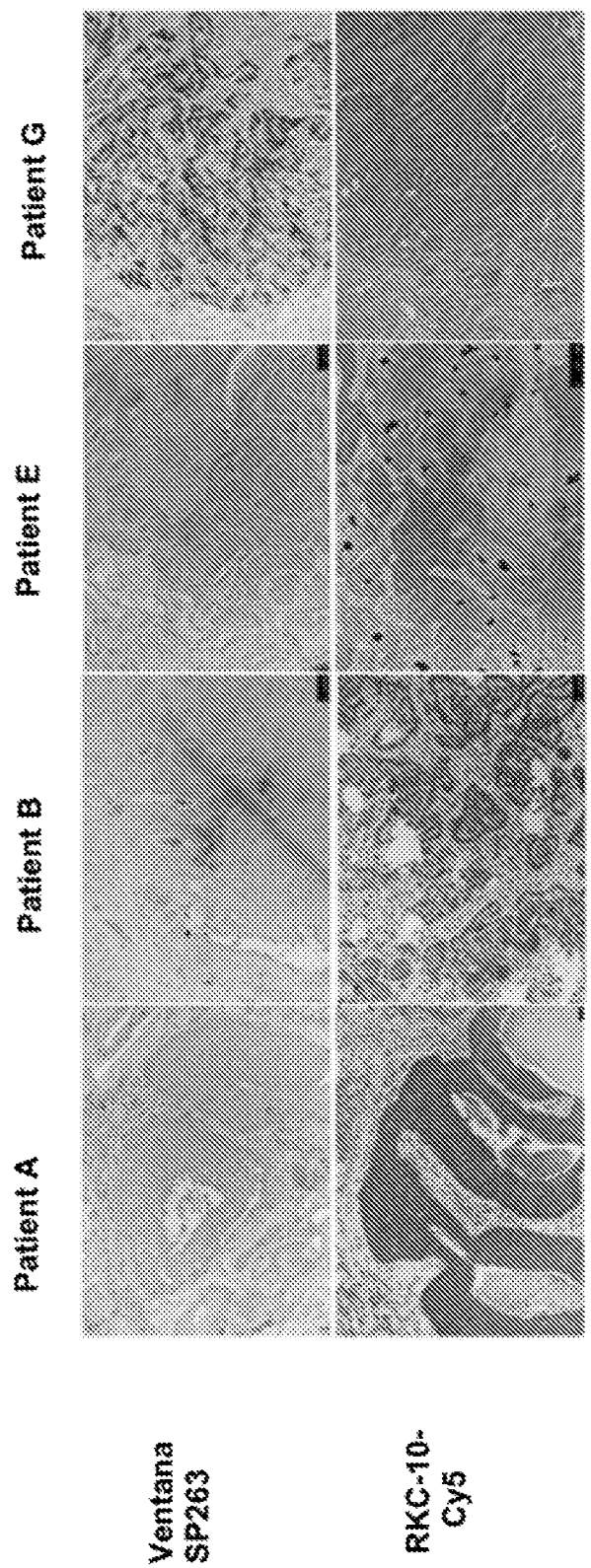
FIG. 9 show that PD-L1 staining was established in repeated placenta tissues in seven NSCLC patient tissues (A-G, not all shown) and was compared with the Ventana SP263 antibody.

Once confidence in PD-L1 staining was established in repeated placenta tissues, staining in seven NSCLC patient tissues (patients 'A' through 'G') was compared with the Ventana SP263 antibody and RK-10-Biotin (FIG. 9). When using the RK-10-Biotin peptide heaviest staining was observed localized to the tumor regions of the tissues, which can be very intense based on the concentration of peptide used. In contrast, the SP263 antibody did not show heavy tumor staining in most tissue sections, showing only faint staining in these regions that could be interpreted as negative or faintly positive for PD-L1. The most intense staining from the SP263 antibody was shown in the tumor cells of patient G. All areas of patient G that stained positive for PD-L1 using the SP263 antibody also stained positively using PD-L1 peptide.

Fluorescent RK-10-Cy5 Detects PD-L1 in NSCLC Patient Tissues and Tissue Microarray.

Figure 10:
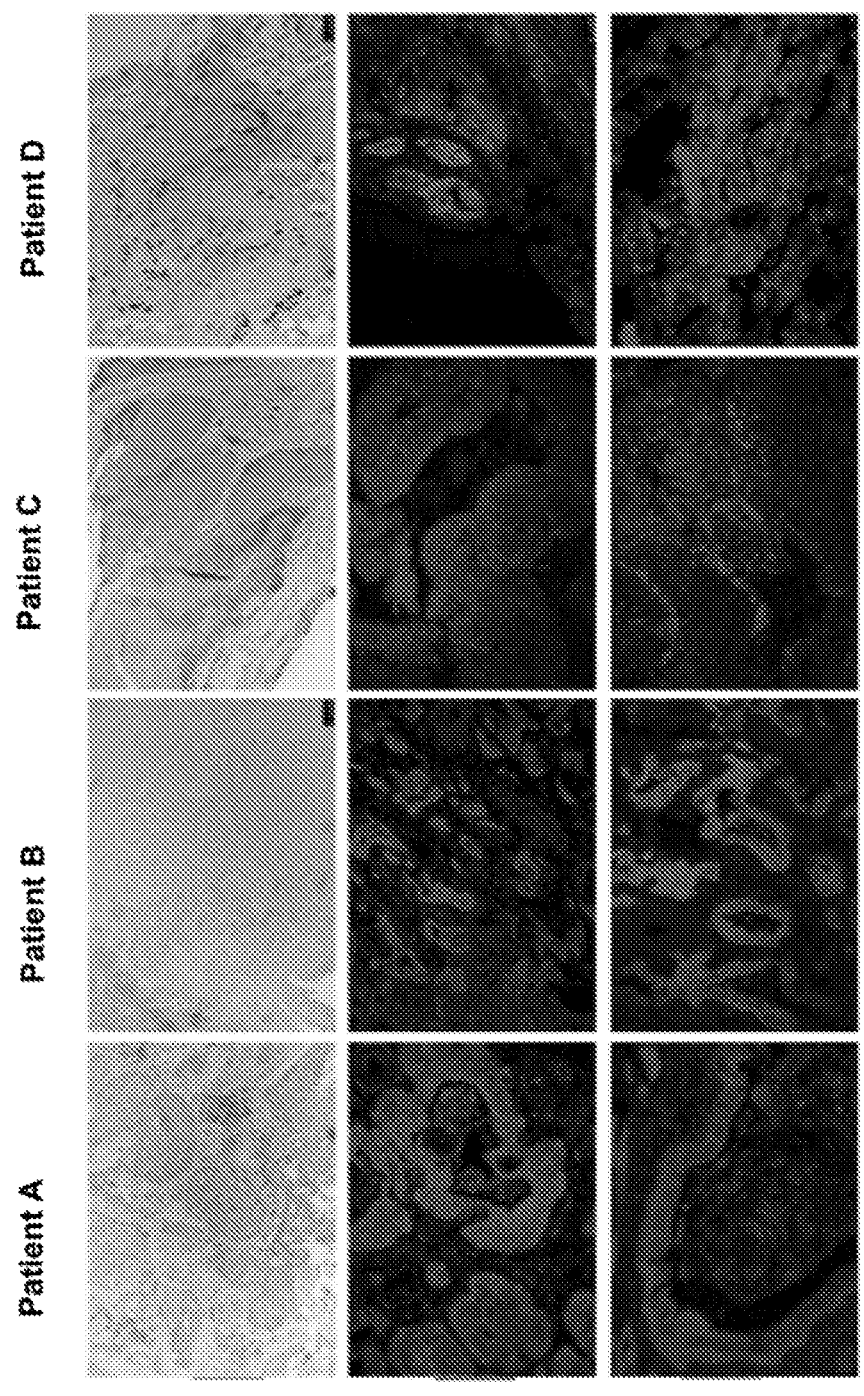
FIG. 10 shows patient tissues A-G (not all shown) stained with RK-10-Cy5.
Figure 11:
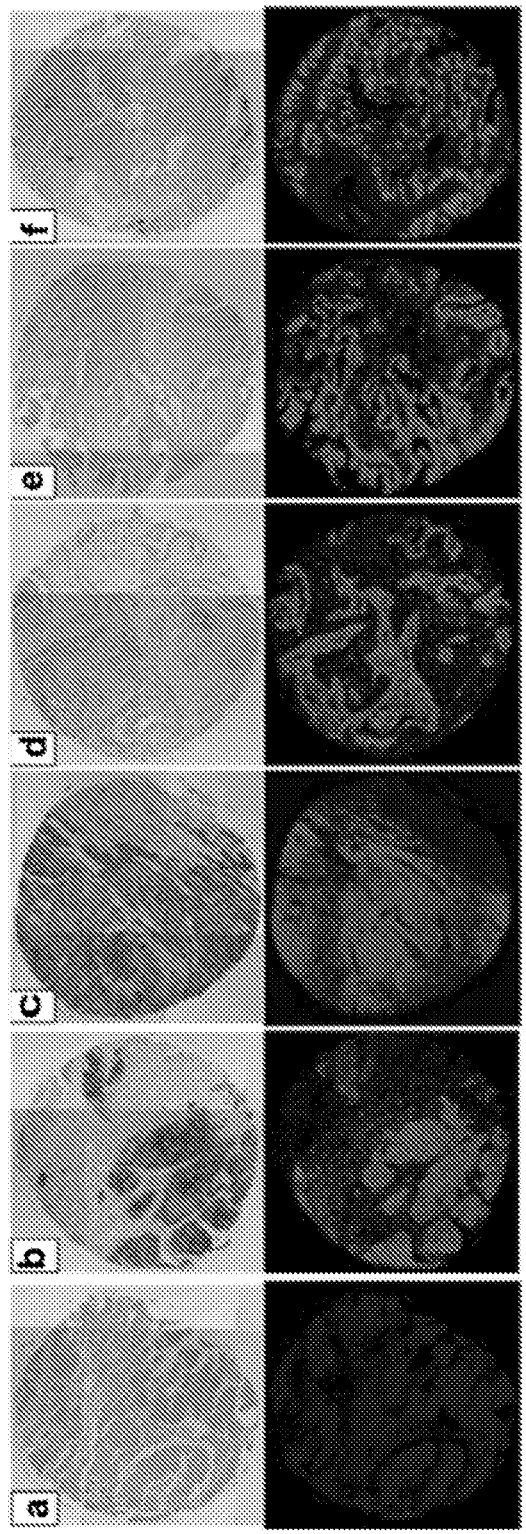
FIG. 11 shows serial sectioned TMAs staining compared head to head with either SP263 kit or the RK-10-Cy5 peptide.
Figure 12:
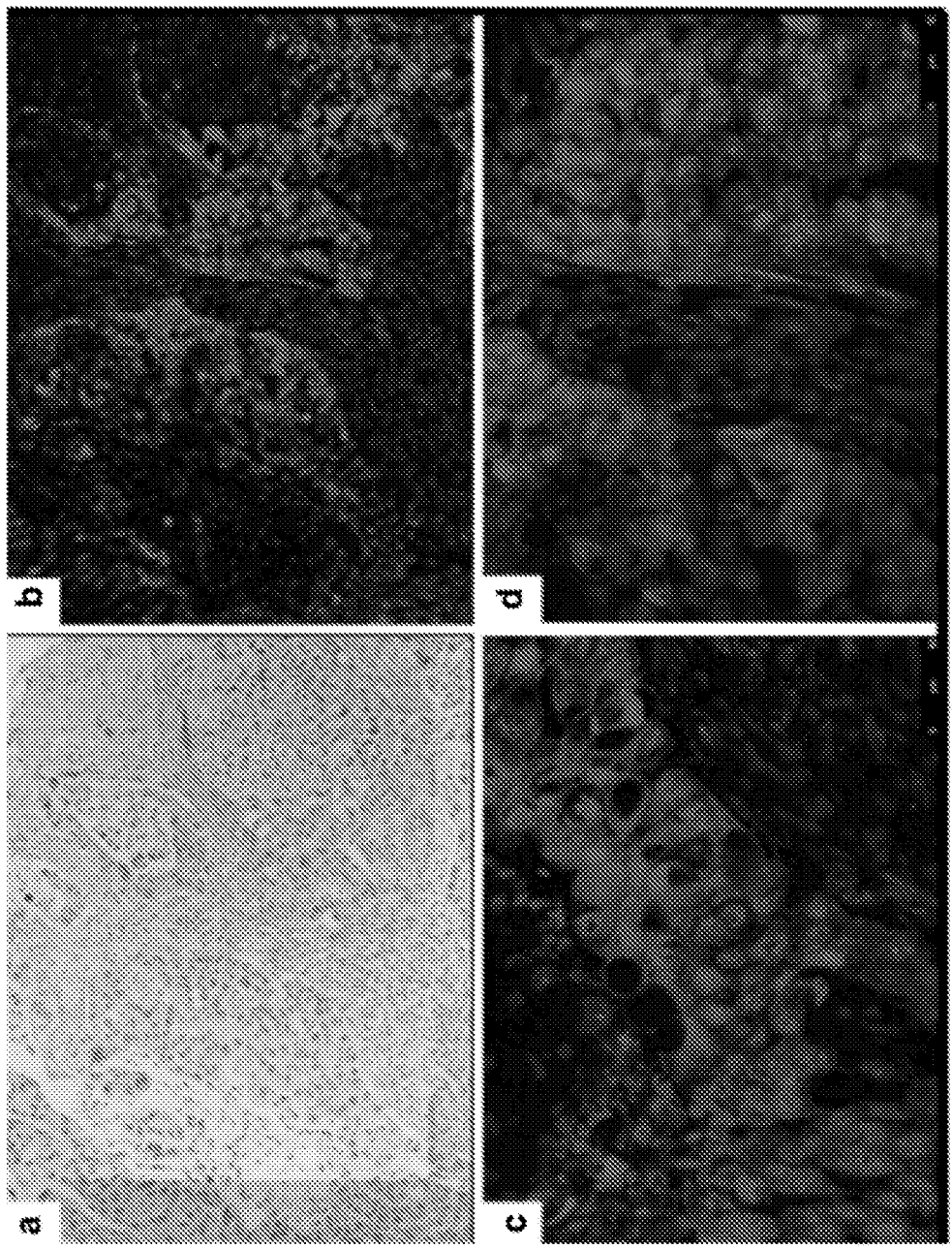
FIG. 12 shows a representative analysis of individual spots at 40× confirming the presence of specific tumor cell staining.
Figure 16:
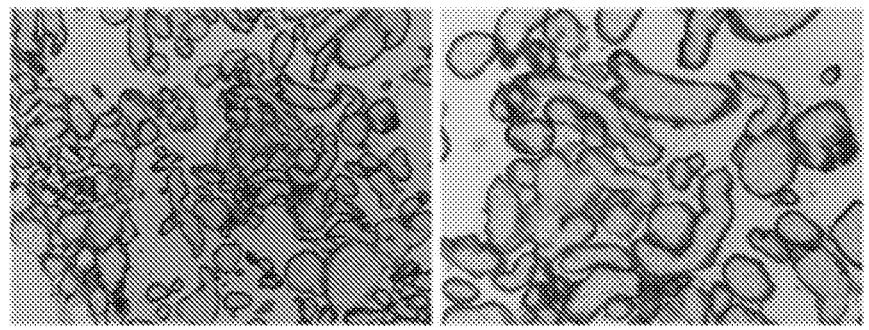
FIG. 16 shows staining of the placental tissue of seven selected NSCLC patient tissues, comparing the Ventana SP263 antibody and RK-10-Cy5.
Figure 16:
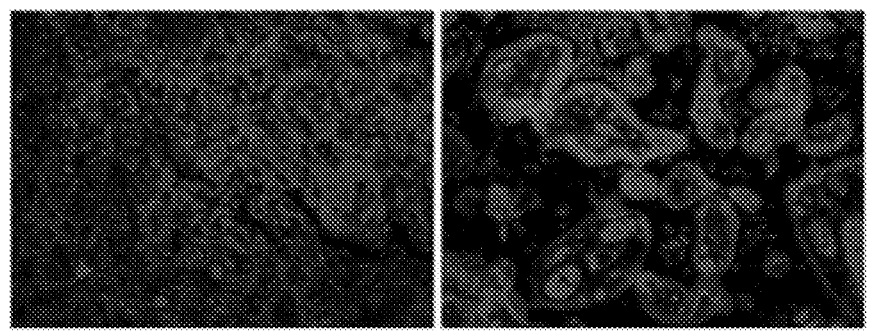
Figure 17:
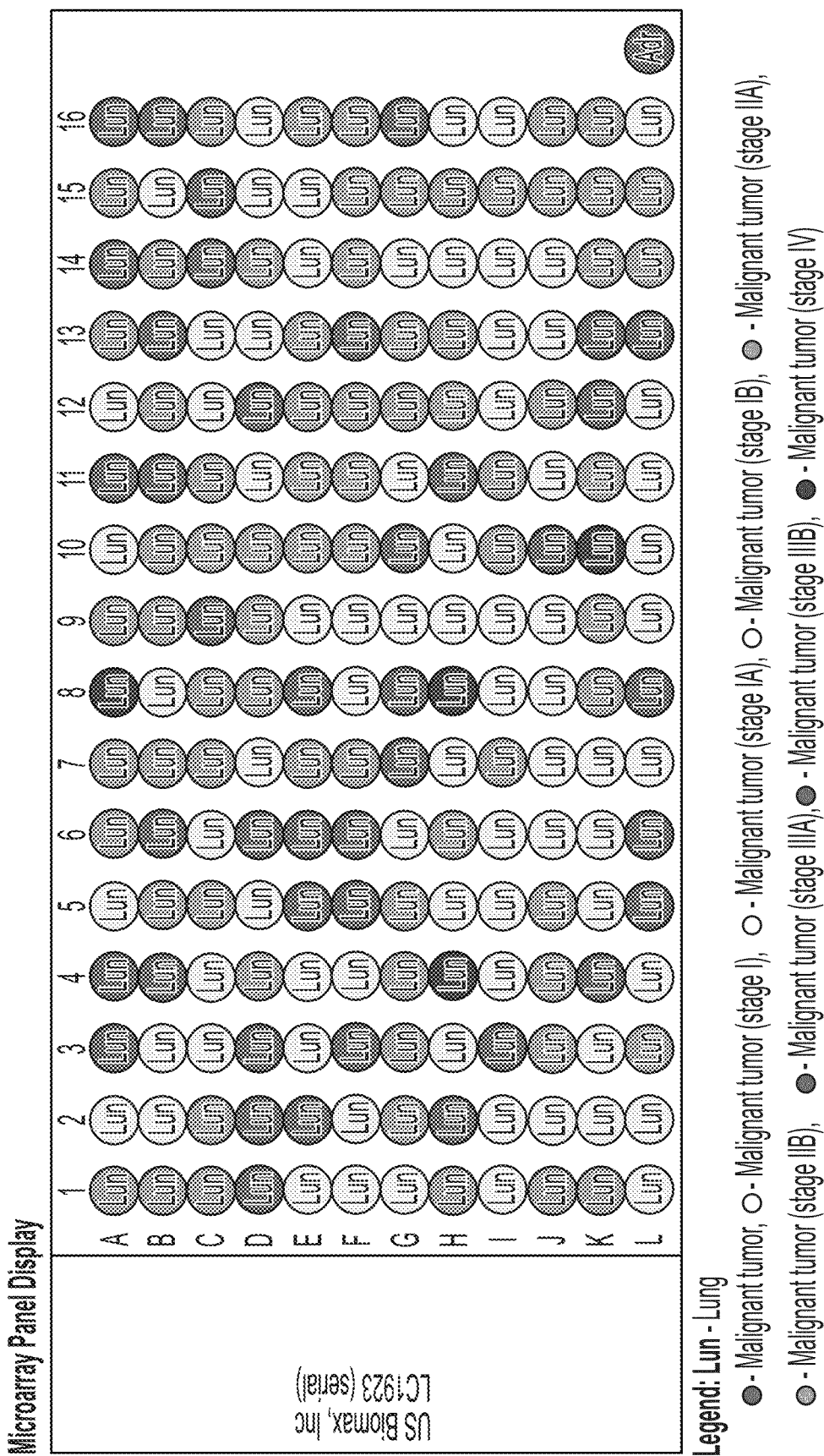
FIG. 17 is a schematic of the layout of a fresh-cut lung cancer tissue microarray.

Staining of the placenta and seven selected NSCLC patient tissues was again compared using the SP263 antibody and RK-10-Cy5 which was conjugated with a Cy5 fluorophore (FIG. 16). To stain with the fluorescent PD-L1 peptide, antigen retrieval was performed and tissue slides were treated with 15 μM fluorescent peptide in a dark, humid chamber for 2 hours, washed with buffer, then counterstained and mounted with DAPI nucleus stain. Peptide-stained slides were imaged on a Leica DM5500 using channels specific for DAPI or Cy5, and channels were overlaid to examine PD-L1 expression. To confirm the data from the IHC stained tissues, the same seven patient tissues A-G were stained with RK-10-Cy5 (FIG. 10). The Cy5 signal in these tissues was consistent with the HRP staining, where RK-10-Cy5 peptide stained many areas of tumor that the SP263 antibody did not. Where the SP263 staining is positive, similar staining between both the antibody and peptide was observed. However, many tumor areas not visibly stained by the antibody were stained specifically when the peptide was used. To examine a larger range of tissues for PD-L1 expression, fresh-cut lung cancer tissue microarrays containing 192 separate cases of lung cancers were purchased from U.S. Biomax, Inc. This array (FIG. 17) contained 78 cases of squamous cell carcinoma, 69 cases of adenocarcinoma, 3 cases of mucinous carcinoma, 7 cases of bronchioalveolar carcinoma, 5 cases of adenosquamous carcinoma, 4 cases of atypical carcinoid, 15 cases of small cell carcinoma, and 11 cases of large cell carcinoma. To analyze stained TMAs, the slides were scanned in at 10× magnification using the Leica DM5500 motorized stage and stitched together using Leica LAS X software. Serial sectioned TMAs were then compared head to head when stained with either SP263 kit or the RK-10-Cy5 peptide (FIG. 11). In cases where the SP263 antibody was negative for tumor staining, the same is seen with the RK-10-Cy5 peptide (FIG. 11, panel a). Likewise, in cases where the SP263 antibody stained positively in tumor, RK-10-Cy5 shows staining consistent with the SP263 stain (FIG. 11, panels b and c). Interestingly, in the majority of cases, the SP263 antibody showed no tumor staining, while the RK-10-Cy5 peptide showed consistent, specific staining in tumor cells and immune infiltrate (FIG. 11, panels d, e, and f). Analysis of individual spots at 40× confirms the presence of specific tumor cell staining (FIG. 12). These results are consistent with the biotin-conjugated peptide IHC, where the PD-L1 peptide stained many large areas of tumor, while the SP263 antibody showed little to no staining in many of these areas. The Cy5 channel was very intensely bright and thus a very low exposure had to be used to image the PD-L1. PD-L1 expression was specifically seen in tumor areas of the tissue, and staining of immune cells was also seen outside the tumor areas, as is expected.

Fluorescent RK-10-Cy5 Detects PD-L1 on Reed-Sternberg Cells in Hodgkin's Lymphoma.

Figure 13:
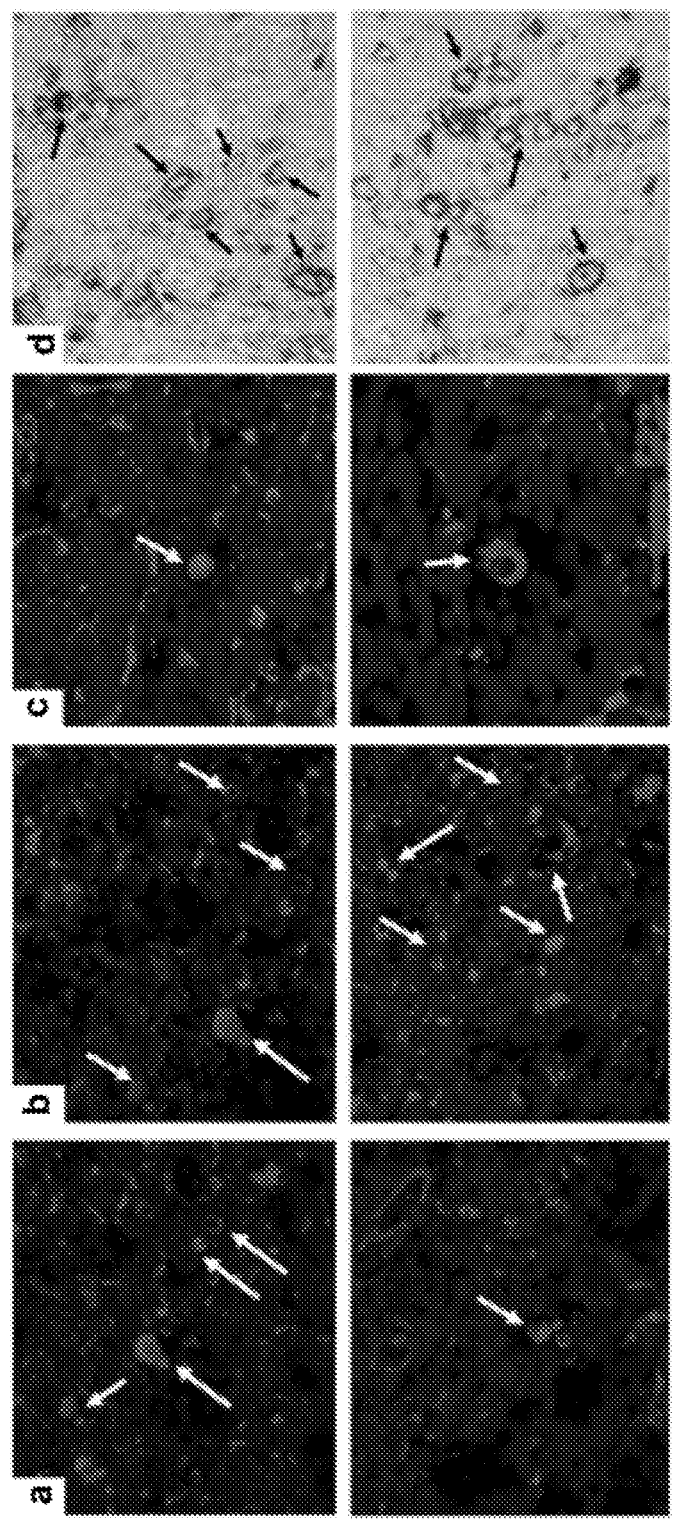
FIG. 13 shows examination of PD-L1 levels in four identified Hodgkin's lymphoma patient samples using the fluorescent RK-10-Cy5 peptide and compared with the SP263 antibody.

In addition to the NSCLC patient tissues, four different Hodgkin's Lymphoma cases for PD-L1 expression were investigated. Presence of Reed-Sternberg cells in a biopsied tissue is often the diagnostic indicator of a patient having Hodgkin's lymphoma. RS cells are large, often multinucleated tumor cells that are derived from B-cell lymphocytes. RS cells heavily express PD-L1 (Chen, B. J. et al. Clinical Cancer Research 19, 3462-3473 (2013)), to the point of PD-L1 being a diagnostic indicator of RS cells. Due to the characteristic expression of PD-L1 in RS cells, PD-L1 levels were examined in the four identified Hodgkin's lymphoma patient samples using the fluorescent RK-10-Cy5 peptide and compared with the SP263 antibody (FIG. 13). In each patient sample, the pathologist-identified RS cells showed PD-L1 staining with both RK-10-Cy5 and SP263 antibody. When using the RK-10-Cy5 peptide, RS cells were easily identified by the pathologist due to the heavy Cy5 fluorescent signal. These cells were additionally confirmed as RS cells by examining the multinucleate characteristic of the cells, shown clearly by staining the nuclei with fluorescent DAPI. The SP263 antibody IHC additionally confirmed the presence of PD-L1 in the RS cells. Using both methods, some light staining of the tumor microenvironment besides the RS cells was observed, which is expected as PD-L1 is often expressed on immune cells.

Discussion

In order to overcome the problems associated with PD-L1 IHC, a novel peptide sequence, RK-10, was developed that is specific for human PD-L1. RK-10 sequence has shown to bind optimally to the structure of PD-1 receptor using crystal structure analysis of the PD-L1:PD1 binding pocket. RK-10 can be modified with reporter molecules of interest, such as biotin for IHC (RK-10-Biotin), or fluorescent molecules for fluorescent analysis (RK-10-Cy5, Cy5). As mentioned above, antibody based IHC agents recognize different epitopes in PD-L1; in sharp contrast, the identified peptide sequence recognizes the unique binding site between PD-1 and PD-L1. Additionally, the peptide based assay developed in this study is standalone, that is secondary antibody is not necessary for staining.

RK-10 Peptide attached with biotin or fluorescent dye enables easy detection of PD-L1 biomarker in tissues and cell lines. The data presented in this study utilizes manual staining of RK-10 in human tissues; therefore, the need for autostainer specific for this agent is unnecessary. Additional advantages include that the peptide is relatively inexpensive, easy to synthesize, and can be mass produced in higher quantities.

The PD-L1 targeting peptide RK-10-Cy5 was identified through structural analysis of PD-1:PD-L1 binding pocket structure. PD-L1 specific peptide RK-10 has shown high sensitivity and specificity for tumor cells in over 200 different cases of tissue—192 lung cancer cases on a TMA, seven patient lung cancers, one placenta tissue, and four Hodgkin's lymphoma cases. Patient tissues stained specifically and reproducibly within the tumor and PD-L1 expressing immune cells using either a biotin-conjugated peptide for IHC, or a Cy5 fluorophore-labelled peptide for fluorescent microscopy. RK-10-Cy5 staining showed a positive correlation with Ventana's FDA-approved PD-L1 diagnostic (SP263) where the SP263 kit stained tumor positively for PD-L1 expression. While there were some cases that were negative using both SP263 and RK-10-Cy5, there were a large number of cases where RK-10-Cy5 showed very specific tumor staining that were not stained by the SP263 antibody. This could either be due to higher sensitivity of RK-10-Cy5 or due to a lower titration of SP263 to only detect PD-L1 above a clinical cutoff, since the SP263 kit is meant for clinical diagnosis for use with its companion therapeutic drug Durvalumab.

In the Hodgkin's lymphoma cases, PD-L1 expression as measured by the RK-10-Cy5 peptide matched up well with the IHC staining shown by the SP263 antibody, especially in the Reed-Sternberg cells. Since pembrolizumab was recently fast-tracked by the FDA to treat Hodgkin's lymphoma cases, RK-10-Cy5 will need to be compared with the pembrolizumab companion diagnostic 22C3. Due to the multinucleate characteristics of the RS cells, it would be easy to detect and quantify the number of RS cells in a given Hodgkin's tissue based on PD-L1 expression and nuclei. Since RK-10-Cy5 shows such specificity for tumor, it could detect a wide range of PD-L1 expression and inform more precise diagnostic levels for treatment. It has been shown that there is an urgent need for a PD-L1 diagnostic that can precisely detect PD-L1 protein irrespective of the drug intended to be used—a sensitive assay such as RK-10-Cy5 could be used to achieve this. Detection of PD-L1 expression in whole blood and metastatic melanoma suggests that RK-10-Cy5 could also potentially be used to detect low amounts of circulating tumor cells that express PD-L1.

Recent debates about the diagnosis of PD-L1 in patients highlight the need for refined methods of determining PD-L1 levels in the patient. By utilizing a peptide-based approach, all levels of PD-L1 can be detected with high sensitivity and specificity. In a heterogeneous tumor, identification of PD-L1 expression using traditional methods may not be an accurate way of determining a binary IHC cutoff, but would rather require a wider range of diagnostic levels to determine optimal therapy. Recent studies have also shown tumors that express PD-L1 according to in vivo imaging methods, but upon excision for IHC no PD-L1 was detected (Ilie, M. et al. *Annals of Oncology* 27, 147-153 (2016)). Tumor mutations over a given period of treatment may lead to fluctuating PD-L1 levels, and as such may need to be monitored routinely.

The PD-L1 specific peptide RK-10 showed high specificity for tumor cells in 200 different cases of tissue—192 lung cancer cases on a TMA, seven patient lung cancers, and one placenta tissue. Patient tissues stained specifically with tumor and PD-L1 expressing immune cells using a biotin-conjugated peptide for IHC or a Cy5 fluorophore-labelled peptide for fluorescent microscopy. RK-10 staining showed a positive correlation with Ventana's PD-L1 diagnostic when Ventana stained tumor positively for PD-L1 expression. While there were some cases that were negative using both Ventana and RK-10, there were a large number of cases where RK-10 showed very specific tumor staining that were not stained by the Ventana antibody. This could either be due to higher specificity of RK-10 or due to a lower titration of Ventana antibody to only detect PD-L1 above a clinical cutoff, since the Ventana kit is meant for clinical diagnosis for use with its therapeutic durvalumab. Since RK-10 shows such specificity for tumor, it could detect a wide range of PD-L1 expression and inform more precise cutoff levels for treatment. Detection of PD-L1 expression in whole blood and metastatic melanoma shows that RK-10 can be used to detect low amounts of circulating tumor cells that express PD-L1. Furthermore, since RK-10 is highly tumor-specific, the peptide could be used for in vivo monitoring of response to clinical therapy directed at PD-L1.

The breadth and scope of the present disclosure should not be limited by any of the above-described exemplary aspects or embodiments, but should be defined only in accordance with the following claims and their equivalents.

PEPTIDE SEQUENCES:
Study Sequences ((GS)$_3$ Spacer)
RK-10:
(SEQ ID NO: 2)
GSGSGSTYLCGAISLAPKAQIKESL RK-10-Biotin:
(SEQ ID NO: 2)
Biotin-GSGSGSTYLCGAISLAPKAQIKESL RK-10-Cy5:
(SEQ ID NO: 2)
Cy5-GSGSGSTYLCGAISLAPKAQIKESL Mock Peptide RK-11:
(SEQ ID NO: 3)
GSGSGSFVLNWYRMSPSNQTDKLAA RK-11-Biotin:
(SEQ ID NO: 3)
Biotin-GSGSGSFVLNWYRMSPSNQTDKLAA -continued RK-11-Cy5:
Cy5-GSGSGSFVLNWYRMSPSNQTDKLAA (SEQ ID NO: 3)

Other Sequences (No Spacer)
High Affinity PD-L1
TYLCGAISLAPKAQIKESL (SEQ ID NO: 1)

Biotin-TYLCGAISLAPKAQIKESL (SEQ ID NO: 1)

Cy5-TYLCGAISLAPKAQIKESL (SEQ ID NO: 1)

Low Affinity 'Mock'
FVLNWYRMSPSNQTDKLAA (SEQ ID NO: 4)

Biotin-FVLNWYRMSPSNQTDKLAA (SEQ ID NO: 4)

Cy5-FVLNWYRMSPSNQTDKLAA (SEQ ID NO: 4)

Scrambled Peptide
LAYTEIKCAGLSPIQALSK (SEQ ID NO: 5)

Biotin-LAYTEIKCAGLSPIQALSK (SEQ ID NO: 5)

Cy5-LAYTEIKCAGLSPIQALSK (SEQ ID NO: 5)

REFERENCES

1. Postow, M. A., Callahan, M. K. & Wolchok, J. D. Immune Checkpoint Blockade in Cancer Therapy. Journal of Clinical Oncology 33, 1974-1982, doi:10.1200/JCO.2014.59.4358 (2015).
2. Tumeh, P. C. et al. PD-1 blockade induces responses by inhibiting adaptive immune resistance. Nature 515, 568-571, doi:10.1038/nature13954 (2014).
3. Bhardwaj, G., Agrawal, A. & Tyagi, R. Combination therapies or standalone interventions? Innovation options for pharmaceutical firms fighting cancer. International Journal of Innovation Management 19, 1540003, doi: 10.1142/s1363919615400034 (2015).
4. La-Beck, N. M., Jean, G. W., Huynh, C., Alzghari, S. K. & Lowe, D. B. Immune Checkpoint Inhibitors: New Insights and Current Place in Cancer Therapy. Pharmacotherapy: The Journal of Human Pharmacology and Drug Therapy 35, 963-976, doi:10.1002/phar.1643 (2015).
5. Zou, W., Wolchok, J. D. & Chen, L. PD-L1 (B7-H1) and PD-1 pathway blockade for cancer therapy: Mechanisms, response biomarkers, and combinations. Science Translational Medicine 8, 328rv324-328rv324, doi:10.1126/scitranslmed.aad7118 (2016).
6. Chen, D. S., Irving, B. A. & Hodi, F. S. Molecular Pathways: Next-Generation Immunotherapy—Inhibiting Programmed Death-Ligand 1 and Programmed Death-1. Clinical Cancer Research 18, 6580-6587, doi:10.1158/1078-0432.ccr-12-1362 (2012).
7. Naidoo, J., Page, D. B. & Wolchok, J. D. Immune Checkpoint Blockade. Hematology/Oncology Clinics of North America 28, 585-600, doi:10.1016/j.hoc.2014.02.002 (2014).
8. Mahoney, K. M., Freeman, G. J. & McDermott, D. F. The Next Immune-Checkpoint Inhibitors: PD-1/PD-L1 Blockade in Melanoma. Clinical Therapeutics 37, 764-782, doi:10.1016/j.clinthera.2015.02.018 (2015).
9. Aguiar, P. N. et al. The role of PD-L1 expression as a predictive biomarker in advanced non-small-cell lung cancer: a network meta-analysis. Immunotherapy 8, 479-488, doi:10.2217/imt-2015-0002 (2016).
10. Garon, E. B. et al. Pembrolizumab for the Treatment of Non-Small-Cell Lung Cancer. New England Journal of Medicine 372, 2018-2028, doi:doi:10.1056/NEJMoa1501824 (2015).
11. Spira, A., et al. in 2015 ASCO Annual Meeting (Journal of Clinical Oncology, Chicago, Ill., 2015).
12. Kerr, K. M. & Hirsch, F. R. Programmed Death Ligand-1 Immunohistochemistry: Friend or Foe? Archives of Pathology & Laboratory Medicine 140, 326-331, doi:10.5858/arpa.2015-0522-SA (2016).
13. Sholl, L. M. et al. Programmed Death Ligand-1 Immunohistochemistry—A New Challenge for Pathologists: A Perspective From Members of the Pulmonary Pathology Society. Archives of Pathology & Laboratory Medicine 140, 341-344, doi:10.5858/arpa.2015-0506-SA (2016).
14. Scheel, A. H. et al. Harmonized PD-L1 immunohistochemistry for pulmonary squamous-cell and adenocarcinomas. Mod Pathol 29, 1165-1172, doi:10.1038/modpathol.2016.117 (2016).
15. Cheng, S., Koch, W. H. & Wu, L. Co-development of a companion diagnostic for targeted cancer therapy. New Biotechnology 29, 682-688, doi:10.1016/j.nbt.2012.02.002 (2012).
16. Kalia, M. Biomarkers for personalized oncology: recent advances and future challenges. Metabolism 64, S16-S21, doi:10.1016/j.metabol.2014.10.027 (2015).
17. Kerr, K. M. et al. Second ESMO consensus conference on lung cancer: pathology and molecular biomarkers for non-small-cell lung cancer. Annals of Oncology 25, 1681-1690, doi:10.1093/annonc/mdu145 (2014).
18. Soliman, H., Khalil, F. & Antonia, S. PD-L1 Expression Is Increased in a Subset of Basal Type Breast Cancer Cells. PLOS ONE 9, e88557, doi:10.1371/journal.pone.0088557 (2014).
19. Usui, Y. et al. Expression of Costimulatory Molecules on Human Retinoblastoma Cells Y-79: Functional Expression of CD40 and B7H1. Investigative Ophthalmology & Visual Science 47, 4607-4613, doi:10.1167/iovs.06-0181 (2006).
20. Chen, N. et al. Upregulation of PD-L1 by EGFR Activation Mediates the Immune Escape in EGFR-Driven NSCLC: Implication for Optional Immune Targeted Therapy for NSCLC Patients with EGFR Mutation. Journal of Thoracic Oncology 10, 910-923, doi:10.1097/JTO.0000000000000500.
21. Veras, E., Kurman, R. J., Wang, T.-L. & Shih, I.-M. PD-L1 Expression in Human Placentas and Gestational Trophoblastic Diseases. International Journal of Gynecological Pathology Publish Ahead of Print, doi:10.1097/pgp.0000000000000305 (9000).
22. Chen, B. J. et al. PD-L1 Expression Is Characteristic of a Subset of Aggressive B-cell Lymphomas and Virus-Associated Malignancies. Clinical Cancer Research 19, 3462-3473, doi:10.1158/1078-0432.ccr-13-0855 (2013).
23. Ilie, M. et al. Comparative study of the PD-L1 status between surgically resected specimens and matched biopsies of NSCLC patients reveal major discordances: a potential issue for anti-PD-L1 therapeutic strategies. Annals of Oncology 27, 147-153, doi:10.1093/annonc/mdv489 (2016).

What is claimed is:

1. A detectably labeled synthetic ligand comprising a peptide or peptidomimetic compound, wherein the peptide or peptidomimetic compound comprises amino acid sidechains following the entire sequential order of the amino acid sequence SEQ ID NO: 1 and wherein the peptide or peptidomimetic compound has a length equal or equivalent to 19 to 39 amino acid residues.

2. The ligand of claim 1, wherein the ligand specifically binds to PD-L1.

3. The ligand of claim 1, wherein the ligand is detectably labeled with a detectable label selected from the group consisting of a fluorescent molecule, a radioisotope, an enzyme conjugate, and a heterologous epitope.

4. The ligand of claim 3, wherein the peptide or peptidomimetic compound is attached to the detectable label via an amino acid spacer $(GS)_n$, wherein n is 2 to 5.

5. The ligand of claim 1, wherein the peptide or peptidomimetic compound has a length equal or equivalent to 19 amino acid residues.

6. The ligand of claim 5, wherein the ligand is a peptide and the peptide and amino acid spacer consist of the amino acid sequence SEQ ID NO: 2 (RK-10 peptide).

7. The ligand of claim 1, wherein the detectable label is biotin or a fluorescent reporter molecule.

8. The ligand of claim 1 selected from the group consisting of the peptide ligand Biotin-$(GS)_3$—SEQ ID NO: 1 (RK-10-Biotin), the peptide ligand Cy5-$(GS)_3$—SEQ ID NO: 1 (RK-10-Cy5), and peptidomimetic compound ligands corresponding to either.

9. A composition comprising the synthetic ligand of claim 1.

10. A method of detecting PD-L1, the method comprising:
    a) contacting a sample with the detectably labeled synthetic ligand of claim 1; and
    b) assaying for the presence of the labeled ligand.

11. The method of claim 10, wherein the sample comprises cells from a subject or a cell line.

12. The method of claim 11, wherein the sample from a subject is blood or a tissue.

13. The method of claim 12, wherein the sample from a subject comprises cancer cells.

14. The method of claim 10, wherein the presence of the labeled ligand is detected via immunohistochemistry or flow cytometry.

15. The method of claim 10, wherein the presence of the labeled ligand is indicative of the amount of PD-L1 expression in the sample or subject and wherein the method further comprises comparing the amount of PD-L1 expression in the sample or subject against a predetermined standard.

16. The method of claim 15, wherein the method further comprises treating the subject's cancer based on the comparison.

17. A method of detecting PD-L1 in a subject, the method comprising the steps of:
    (a) administering the detectably labeled synthetic ligand of claim 1 to the subject; and
    (b) assaying for the presence of the labeled ligand in said subject.

18. The method of claim 17, wherein the location of the labeled ligand in the subject is visualized.

19. The method of claim 18, wherein the location of the labeled ligand is indicative of a cancer tumor and the method further comprises treating the subject's cancer based on the location of the tumor.

20. A method of making a detectably labeled synthetic ligand for detecting PD-L1, the method comprising incorporating a detectable label into, or attaching either directly or via a spacer a detectable label to, a peptide or peptidomimetic compound that comprises amino acid sidechains following the entire sequential order of the amino acid sequence SEQ ID NO: 1, wherein the peptide or peptidomimetic compound has a length equal or equivalent to 19 to 39 amino acid residues.

* * * * *

SEQUENCE LISTING

<160> NUMBER OF SEQ ID NOS: 5

<210> SEQ ID NO 1
<211> LENGTH: 19
<212> TYPE: PRT
<213> ORGANISM: Homo sapiens

<400> SEQUENCE: 1

Thr Tyr Leu Cys Gly Ala Ile Ser Leu Ala Pro Lys Ala Gln Ile Lys
1               5                   10                  15

Glu Ser Leu

<210> SEQ ID NO 2
<211> LENGTH: 25
<212> TYPE: PRT
<213> ORGANISM: Artificial Sequence
<220> FEATURE:
<223> OTHER INFORMATION: Synthetic

<400> SEQUENCE: 2

Gly Ser Gly Ser Gly Ser Thr Tyr Leu Cys Gly Ala Ile Ser Leu Ala
1               5                   10                  15

Pro Lys Ala Gln Ile Lys Glu Ser Leu
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic

<400> SEQUENCE: 3

Gly Ser Gly Ser Gly Ser Phe Val Leu Asn Trp Tyr Arg Met Ser Pro
1               5                   10                  15

Ser Asn Gln Thr Asp Lys Leu Ala Ala
            20                  25

<210> SEQ ID NO 4
<211> LENGTH: 19
<212> TYPE: PRT
<213> ORGANISM: Homo sapiens

<400> SEQUENCE: 4

Phe Val Leu Asn Trp Tyr Arg Met Ser Pro Ser Asn Gln Thr Asp Lys
1               5                   10                  15

Leu Ala Ala

<210> SEQ ID NO 5
<211> LENGTH: 19
<212> TYPE: PRT
<213> ORGANISM: Artificial Sequence
<220> FEATURE:
<223> OTHER INFORMATION: Synthetic

<400> SEQUENCE: 5

Leu Ala Tyr Thr Glu Ile Lys Cys Ala Gly Leu Ser Pro Ile Gln Ala
1               5                   10                  15

Leu Ser Lys